(12) United States Patent
Mohanty

(10) Patent No.: US 9,006,204 B2
(45) Date of Patent: Apr. 14, 2015

(54) APTAMERS FOR PRION DIAGNOSTICS AND APTAMER BINDING DETECTION SYSTEM

(71) Applicant: Sarina Mohanty, Pasadena, CA (US)

(72) Inventor: Sarina Mohanty, Pasadena, CA (US)

(73) Assignee: Aptrix LLC, New York, NY (US)

(*) Notice: Subject to any disclaimer, the term of this patent is extended or adjusted under 35 U.S.C. 154(b) by 0 days.

(21) Appl. No.: 13/935,423

(22) Filed: Jul. 3, 2013

(65) Prior Publication Data

US 2014/0011209 A1 Jan. 9, 2014

Related U.S. Application Data

(60) Provisional application No. 61/668,023, filed on Jul. 4, 2012.

(51) Int. Cl.
*C12N 15/115* (2010.01)
*G01N 33/68* (2006.01)
*G01N 33/53* (2006.01)

(52) U.S. Cl.
CPC .......... *C12N 15/115* (2013.01); *G01N 33/6896* (2013.01); *G01N 33/5308* (2013.01); *G01N 2800/2828* (2013.01); *C12N 2310/16* (2013.01)

(58) Field of Classification Search
None
See application file for complete search history.

(56) References Cited

U.S. PATENT DOCUMENTS

| | | | |
|---|---|---|---|
| 5,071,745 A | 12/1991 | Triscott | |
| 5,196,306 A | 3/1993 | Bobrow | |
| 5,998,149 A | 12/1999 | Hsich | |
| 8,324,357 B2 | 12/2012 | Chelyapov | |
| 2003/0162225 A1 | 8/2003 | James | |
| 2004/0161758 A1 | 8/2004 | Seiwert | |
| 2010/0069468 A1* | 3/2010 | Hess et al. | 514/44 R |

OTHER PUBLICATIONS

Simon et al., "Rapid Typing of Transmissible Spongiform Encephalopathy Strains with Differential ELISA" Emerging Infectious Diseases 14:(4):608-616, 2008.
Weber et al., "Cell-free formation of misfolded prion protein with authentic prion infectivity" PNAS, 103:15818-15823, 2006.
Kal'nov et al., "Isolation and Characterization of Full-Length Recombinant Cattle PrPC Protein" Bull. Exp. Biol. Med. 141:62-65, 2006.
DI Giusto et al. "Construction, Stability, and Activity of Multivalent Circular Anticoagulant Aptamers", J. Biol. Chem. 279:46483-46489, 2006.
Stojanovic et al. "Aptamer-Based Folding Fluorescent Sensor for Cocaine" J. Am. Chem. Soc. 123:4928-4931, 2001.
Dyke et al., "First-in-Human Experience of an Antidote-Controlled Anticoagulant Using RNA Aptamer Technology" Circulation 2006;114;2490-2497.
Stojanovics et al., "Aptamer-Based Colorimetric Probe for Cocaine" J. Am. Chem. Soc. 124:9678-9679, 2002.
Castilla et al., "Detection of prions in blood" Nature Med. 11(9):928-986, 2005.
Bieschke et al. "Ultrasensitive detection of pathological prion protein aggregates by dual-color scanning for intensely fluorescent targets" PNAS 97:5468-5473, 2000.
O'Donovan et al. "Prion Protein Fragment PrP-(106-126) Induces Apoptosis via Mitochondrial Disruption in Human Neuronal SH-SY5Y Cells" J. Biol. Chem. 276(47):43516-43523, 2001.
Ellington et al., "In vitro selection of RNA molecules that bind specific ligands" Nature 346:818-822, 1990.
Proske et al., "Prion-Protein-Specific Aptamer Reduces PrPSc Formation" ChemBioChem 2002, 3, 717 ± 725.
Vinkenborg et al., "Aptamers for allosteric regulation" Nature Chem. Biol. 7:519-527, 2011.
Grassi et al., "Progress and limits of TSE diagnostic tools" Vet. Res. (2008) 39:33.
Collen et al., "Primary Structure of Human Fibrinogen and Fibrin" J. Biol. Chem. 250:5808-5817, 1975.
Kim et al., "Sequence Determinants of Enhanced Amyloidogenicity of Alzheimer A42 Peptide Relative to A40" J. Biol. Chem. 280:35069-35076, 2005.
Kouassi et al., "A nanoparticle-based immobilization assay for prion-kinetics study" J. Nanotachnology 4:8, 2006.
Castilla et al. 1, "In Vitro Generation of Infectious Scrapie Prions" Cell, 121:195-206, 2005.
Gofflot et al., "Immunoquantitative PCR for Prion Protein Detection in Sporadic Creutzfeldt—Jakob Disease" Clin. Chem. 51:1605-1611, 2005.
Kuwata et al., "NMR-detected hydrogen exchange and molecular dynamics simulations provide structural insight into fibril formation of prion protein fragment 106-126" PNAS 100:14790-14795, 2003.
Lee et al., "A therapeutic aptamer inhibits angiogenesis by specifically targeting the heparin binding domain of VEGF165" PNAS 102:18902-18907, 2005.
Li et al., "Molecular Aptamer Beacons for Real-Time Protein Recognition" Biochem. Biophys Res. Comm. 292:31=40, 2002.
Legname et al., "Strain-specified characteristics of mouse synthetic prions" PNAS 102:2168-2173, 2005.
Kaesermamnn et al., "Sodium hydroxide renders the prion protein PrPSc sensitive to proteinase K" J. Gen. Virol. 84:3173-3176, 2003.

(Continued)

*Primary Examiner* — Tracy Vivlemore
(74) *Attorney, Agent, or Firm* — Jeffrey B. Oster

(57) ABSTRACT

There is disclosed PrP$^{Sc}$ aptamers. There is further disclosed PrP$^{Sc}$ aptamers. There is further disclosed an infectious agent or neurodegenerative disease bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end.

6 Claims, 9 Drawing Sheets

(56) References Cited

OTHER PUBLICATIONS

Chelyapov, "Allosteric Aptamers Controlling a Signal Amplification Cascade Allow Visual Detection of Molecules at Picomolar Concentrations" Biochemistry 45:2461-2466, 2006.
Strachnan et al., "A sensitive microsphere coagulation ELISA for *Escherichia coli* O157:H7 using Russell's viper venom" Microbiol. Lett. 186:79-84, 2000.
Chen et al., "Zymogenic and enzymatic properties of the 70-80 loop mutants of factor X/Xa" Protein Sci. 13:431-442, 2004.
Zou et al., "Antibody to DNA detects scrapie but not normal prion protein" PNAS 101:1380-1385, 2004.
Ho et al., "Folding Very Short Peptides Using Molecular Dynamics" PLOS Computational Biol. 2(4): e27.2006.
Rahimi et al., "RNA Aptamers Generated against Oligomeric Ab40 Recognize Common Amyloid Aptatopes with Low Specificity but High Sensitivity" PLoS ONE 4(11): e7694, 2009.
Saa et al. "Ultra-efficient Replication of Infectious Prions by Automated Protein Misfolding Cyclic Amplification" J. Biol. Chem. 281:35245-35252, 2006.
Saborio et al., "Sensitive detection of pathological prion protein by cyclic ampli® cation of proteinmisfolding" Nature 411:810-814, 2001.
Krishnaswamy "Prothrombinase Complex Assembly" J. Biol. Chem. 265:3708-3718, 1990.
Degioia et al. "Conformational Polymorphism of the Amyloidogenic and Neurotoxic Peptide Homologous to Residues 106-126 of the Prion Protei" J. Biol. Chem. 269:7859-7862, 1994.
King et al., "Thioaptamer Interactions with Prion Proteins: Sequence-specific and Non-specific Binding Sites" J. Mol. Biol. 369:1001-1014, 2007.
Cox et al. "Automated selection of aptamers against protein targets translated in vitro: from gene to aptamer" Nucl. Acids Res. 30:e108, 2002.
Tahiri-Alaoui et al. "Competing intrachain interactions regulate the formation of -sheet fibrils in bovine PrP peptides" Protein Sci. 12:600-608, 2003.
Long et al., "Crystal structure of an RNA aptamer bound to thrombin" RNA 14:2504-2512, 2008.
Saa et al. 1 "Presymptomatic Detection of Prions in Blood" Science 313:92-94, 2006.
Castilla et al.2 "Crossing species barrier by PrPSc replication in vitro generates new infectious prions" Cell 134:757-768, 2008.
Jan et al. "The Ratio of Monomeric to Aggregated Forms of Aβ40 and Aβ42 is an Important Determinant of Amyloid-β Aggregation, Fibrillogenesis, and Toxicity" J. Biol. Chem. 283(42): 28176-28189, 2008.
LeVine, "Thioflavine T interaction with synthetic Alzheimer's disease (@-amyloid peptides: Detection of amyloid aggregation in solution" Protein Sci. 2:404-410, 1993.
Fox et al. "Approaching the Golden Age of Natural Product Pharmaceuticals from Venom Libraries: An Overview of Toxins and Toxin-Derivatives Currently Involved in Therapeutic or Diagnostic Applications" Curr. Pharma. Design 13:2927-2934, 2007.
Bell et al., "RNA Molecules That Bind to and Inhibit the Active Site of a Tyrosine Phosphatase" J. Biol. Chem. 273:14309-14314, 1998.
Trieschmann et al., "Ultra-sensitive detection of prion protein fibrils by flow cytometry in blood from cattle affected with bovine spongiform encephalopathy" BMC Biotechnology 2005, 5:26.
Ruchman et al., "2-Fluoropyrimidine RNA-based Aptamers to the 165-Amino Acid Form of Vascular Endothelial Growth Factor (VEGF165)" J. Biol. Chem. 273:20556-20567, 1998.
Zhang et al. "Visual Cocaine Detection with Gold Nanoparticles and Rationally Engineered Aptamer Structures" small 2008, 4, No. 8, 1196-1200.
Wilson et al., "In Vitro Selection of Functional Nucleic Acids" Annu. Rev. Biochem. 68:611-647, 1999.
Rhie et al., "Characterization of 2-Fluoro-RNA Aptamers That Bind Preferentially to Disease-associated Conformations of Prion Protein and Inhibit Conversion" J. Biol. Chem. 2003, 278:39697-39705.
Sayer et al., "Structural Determinants of Conformationally Selective, Prion-binding Aptamers" J. Biol. Chem. 2004, 279:13102-13109.
Smith, Robert L. "Titration of activated bovine factor X." Journal of Biological Chemistry 248.7 (1973): 2418-2423.
McGee, Maria P., and H. E. N. R. Y. Rothberger. "Assembly of the prothrombin activator complex on rabbit alveolar macrophage high-affinity factor Xa receptors. A kinetic study." The Journal of experimental medicine 164.6 (1986): 1902-1914.
Bennion, Brian J., and Valerie Daggett. "Protein conformation and diagnostic tests: The prion protein." Clinical chemistry 48.12 (2002): 2105-2114.
Lu, Q., J. M. Clemetson, and K. J. Clemetson. "Snake venoms and hemostasis." Journal of Thrombosis and Haemostasis 3.8 (2005): 1791-1799.
Lau, Anthony L., et al. "Characterization of prion protein (PrP)-derived peptides that discriminate full-length PrPSc from PrPC." Proceedings of the National Academy of Sciences 104.28 (2007): 11551-11556.
Fukae et al., "Females exhibit more extensive amyloid, but not tau,pathology in an Alzheimer transgenic model" Brain Res., 1216:92-103, 2008.
Orru et al., "Prion Disease Blood Test Using Immunoprecipitation and Improved Quaking-Induced Conversion" MBio, 2:0078-11, 2011.
Numao et al., "Novel Biological Activity of the Region (106-126) on Human Prion Sequence" Biol. Pharm. Bull. 26(2) 229-232 (2003).
Florio, Tullio, et al. "Contribution of two conserved glycine residues to fibrillogenesis of the 106-126 prion protein fragment. Evidence that a soluble variant of the 106-126 peptide is neurotoxic." Journal of neurochemistry 85.1 (2003): 62-72.
Yoshida, Wataru, Koji Sode, and Kazunori Ikebukuro. "Aptameric enzyme subunit for biosensing based on enzymatic activity measurement." Analytical chemistry 78.10 (2006): 3296-3303.
Anderson, Maighdlin, et al. "Polymorphism and ultrastructural organization of prion protein amyloid fibrils: an insight from high resolution atomic force microscopy." Journal of molecular biology 358.2 (2006): 580-596.
Wu, Lihong, and James F. Curran. "An allosteric synthetic DNA." Nucleic acids research 27.6 (1999): 1512-1516.
Cong, Xiangyu, and Marit Nilsen-Hamilton. "Allosteric aptamers: targeted reversibly attenuated probes." Biochemistry 44.22 (2005): 7945-7954.
Freire, Ernesto. "Can allosteric regulation be predicted from structure?." Proceedings of the National Academy of Sciences 97.22 (2000): 11680-11682.
Zhu, Lei, and Eric V. Anslyn. "Signal amplification by allosteric catalysis." Angewandte Chemie International Edition 45.8 (2006): 1190-1196.
Liu, Juewen, Zehui Cao, and Yi Lu. "Functional nucleic acid sensors." Chemical reviews 109.5 (2009): 1948-1998.
Wang et al., "Bacterial Inclusion Bodies Contain Amyloid-Like Structure" Plos Bio 6:1791-1801, 2008.
Gonzalez-Montalban et al., "Highly Efficient Protein Misfolding Cyclic Amplification" Plos Path. 7:1001277, 2011.
Chang, Binggong, et al. "Test for detection of disease-associated prion aggregate in the blood of infected but asymptomatic animals." Clinical and Vaccine immunology 14.1 (2007): 36-43.
Gopinath, Subash CB, et al. "An RNA aptamer that discriminates bovine factor IX from human factor IX." Journal of biochemistry 140.5 (2006): 667-676.

* cited by examiner dG = -8.70 [Initially -8.70] seq 74_10_5 dG = -5.70 [Initially -5.70] B-end second seq component

Figure 9A - FLfus74 to RVV-X

Figure 9B - Fus74_10_5 to RVV-X

Figure 9C – B-end to alpha-Thrombin

APTAMERS FOR PRION DIAGNOSTICS AND APTAMER BINDING DETECTION SYSTEM

CROSS REFERENCE TO RELATED APPLICATION

This patent application claims priority to U.S. Provisional Patent application 61/668,023 filed 4 Jul. 2012.

TECHNICAL FIELD

The present disclosure provides $PrP^{Sc}$ aptamers. In particular, the disclosure provides protease resistant and nuclease resistant $PrP^{Sc}$ aptamers. The $PrP^{Sc}$ aptamers are used in diagnostic tests for determining the presence of $PrP^{Sc}$ in CNS tissue or even from live animal blood samples. The present disclosure further provides an infectious agent bifunctional aptamer comprising a first sequence component, and a second sequence component. The present disclosure further provides a method for determining the presence of infectious prion $PrP^{Sc}$ using an infectious agent bifunctional aptamer comprising a first sequence component, and a second sequence component. The present disclosure further provides a component for detecting the presence of an agent configured in a bifunctional aptamer comprising a first sequence component, and a second sequence component.

BACKGROUND

Transmissible spongiform encephalopathies (TSEs) are a heterogeneous group of fatal neurodegenerative disorders that occur in humans, ruminant herbivores, mink, and cats. Sheep scrapie is the prototype of this group. TSEs are characterized by deposition of prion proteins (also denoted as PrP-Scrapie or $PrP^{Sc}$, the infectious form of the proteins), in the central nervous system of affected individuals. Prions have been defined as small proteinaceous infectious particles which resist inactivation by procedures that modify nucleic acids. The term "prion" is a contraction of the words "protein" and "infection," and prions are comprised largely if not exclusively of PrP-Sc molecules encoded by a PrP gene. Prion diseases are often called spongiform encephalopathies because of the post mortem microscopic or histopathologic appearance of the brain of an infected animal with large vacuoles in the cortex and cerebellum. Prion proteins are insoluble, protease-resistant glycoproteins resulting from post translational modification of normal mammalian glycoproteins (PrP-Cellular or PrP-C). Deposition of the prion protein, an abnormal isoform of a native cellular sialoglycoprotein, in the central nervous system is a reliable marker of TSE infection.

The most widely studied TSEs in food-producing animals include scrapie in sheep and goats, bovine spongiform encephalopathy (BSE) in cattle (also known as "Mad Cow" disease), and chronic wasting disease (CWD) in mule deer and elk. Other TSEs in animals include transmissible mink encephalopathy (TME) in mink and feline spongiform encephalopathy (FSE) in cats. Prion diseases of humans have also been identified, which include: Creutzfeldt-Jakob Disease (CJD); Gerstmann-Straussler-Scheinker Syndrome (GSS); Fatal Familial Insomnia (FFI); Alper's Syndrome, and Kuru.

The transmissible agent in these diseases remains controversial. It appears that the scrapie isoform of the prion protein (PrP-Sc or $PrP^{Sc}$) is necessary for both the transmission and pathogenesis of the transmissible neurodegenerative diseases of animals and humans (see Prusiner, *Science,* 252, 1515-1522, 1991).

A new clinical version of CJD in humans is believed to be the result of transfer of BSE from cattle to humans. This finding led to the conclusion that variant CJD was caused by infection of humans with prions from BSE infected cattle. Furthermore, the incidence and timing of the appearance of variant CJD cases opened the possibility that a considerable number of humans, presently free of clinical symptoms, could be latent for the disease. Given that CJD might pass from human to human in infected blood, it can be assumed that humans infected with variant CJD contain the infectious agent in their blood. A potentially infectious species specific agent has been discovered in blood of humans with CJD, cattle with BSE, and sheep with scrapie. ELISA tests have been developed that detect these TSE specific proteins that are associated with $PrP^{Sc}$ ("Prion associated proteins") in the blood of animals and humans. Prion associated proteins are expressed in a disease specific manner in all subjects with clinical symptoms of BSE ("BSAS"), scrapie ("SCRAPAS") and CJD ("CJD"). Prion associated proteins appear to have the chemical characteristics for binding to PrP-C and converting it to $PrP^{Sc}$, and thus are most likely the infectious agents in TSE diseases. Furthermore, expression of prion associated proteins in a subject is accompanied by expression of specific anti-prion associated protein endogenous antibody. Detecting this endogenous antibody in human blood and blood products is the basis of some TSE ELISA tests (U.S. Pat. No. 6,350,854).

The occurrence of novel transmissible spongiform encephalopathies in cattle in the United Kingdom and Europe, and in mule deer and elk in parts of the United States has emphasized the need for reliable diagnostic tests. Further, the epizootic of a TSE in cattle and its postulated relationship to a new variant of human Creutzfeldt Jakob Disease have increased public and scientific awareness of these relatively rare disorders, and have highlighted the need for preclinical detection of TSEs. Accordingly, sensitive immunohistochemical techniques and preclinical detection methods are necessary for the detection, surveillance, and control of TSEs.

Confirmation of TSEs is accomplished by postmortem microscopic or histological examination of brain tissue of suspected cases. Postmortem histopathologic diagnosis of the ruminant TSEs is based on the appearance of neuronal vacuolation, spongiform changes, gliosis, and astrocytosis. However, these can vary in intensity and anatomic location depending on the host species, the individuals, host genetics, stage of disease, and infectious source. Thus, diagnosis by histopathology alone may be equivocal in early cases and usually not possible in autolyzed tissue.

Monoclonal antibody 263K 3F4 (U.S. Pat. No. 4,806,627) detects $PrP^{Sc}$ in hamsters and humans, and has received use in diagnostic assays and pathogenesis studies of human TSEs. Ante-mortem testing in humans with suspected CJD is performed by immunohistochemical and histologic examination of brain biopsies. Because brain biopsy in ruminant animals is not feasible, an alternative approach has been to biopsy selected lymph nodes.

Therefore, there exists a need for a practical, inexpensive, and more rapid method for detection of prion proteins, prion-associated proteins and peptides and/or their respective host antibodies in live animals or humans. In addition, there exists a need for sensitive diagnostic assays to detect prion and prion associated proteins and peptides and/or their respective host antibodies in animal tissues and animal by-products in a most rapid fashion to minimize quarantine time.

Aptamers are functional synthetic nucleic acids useful for high-affinity binding to targets (e.g., nucleic acids, proteins, and chemical compounds). Unlike naturally occurring nucleic acids, which transfer genetic information, aptamers are selected on the basis of their ability to specifically bind their ligand. The specificity of binding is defined in terms of the dissociation constant $K_d$ of the aptamer for its ligand. Aptamers can have high affinity with $K_d$ range similar to antibody (pM to nM) and specificity similar/superior to antibody (Tuerk and Gold, *Science*, 249:505, 1990; Ellington and Szostak, *Nature*, 346:818, 1990).

Many aptamers have a stem-loop structure in which the bases in the loop and the stem are intimately involved in interaction with the ligand. RNA aptamers have been isolated against the protease-sensitive, N-terminus of PrP (Weiss et al., *J. Virol.* 71:8790-8797, 1997) but these do not discriminate between $PrP^C$ and $PrP^{Sc}$ and are sensitive to nucleases. Therefore, there is a need in the art to design and utilize aptamers for binding to specifically folded prions, specifically those prions that are infectious and disease-causing in animals/mammals, in order to prevent the transmission and spread of such diseases in the food supply. The present disclosure provides improved aptamers for detecting the presence of $PrP^{Sc}$ where the aptamers are not sensitive to nucleases.

SUMMARY

The present disclosure provides $PrP^{Sc}$ aptamers. In particular, the disclosure provides protease- and nuclease-resistant $PrP^{Sc}$ aptamers. The $PrP^{Sc}$ aptamers are used in diagnostic tests for determining the presence of $PrP^{Sc}$ in CNS tissue or even from live animal blood samples. The present disclosure further provides an infectious agent bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. The present disclosure provides a neurodegenerative disease bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. The present disclosure provides a method for determining the presence of infectious prion $PrP^{Sc}$ using an infectious agent bifunctional aptamer having comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. The present disclosure further provides a component for detecting the presence of an agent configured in a bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to an agent, and wherein the second sequence component sequence is inserted into the first sequence component from 1 to 5 bases from the 5' end.

The present disclosure further provides an infectious agent bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. Preferably, the infectious agent is selected from the group consisting of $PrP^C$, $PrP^{Sc}$, Transmissible spongiform encephalopathies (TSEs), Creutzfeldt-Jacob disease (CJD), variant CJD (vCJD), bovine spongiform encepathy (BSE) and scrapie. Preferably, the infectious agent is $PrP^{Sc}$ and the sequence of the second sequence component is SEQ ID NO. 90.

The present disclosure provides a neurodegenerative disease bifunctional aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. Preferably, the first sequence component is selected from the group consisting of SEQ ID NOs 1-10, 70 and 74. Preferably, the neurodegenerative disease is selected from the group consisting of Alzheimer's Disease, mild cognitive impairment, Parkinson's disease, and other neurodegenerative diseases. Preferably, the neurodegenerative disease is Alzheimer's Disease and the sequence of the second sequence component is SEQ ID NO. 91.

The present disclosure provides a method for determining the presence of infectious prion $PrP^{Sc}$ using an infectious agent bifunctional aptamer having comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to a specific infectious agent, and wherein the second sequence component sequence is inserted into the first sequence component from 1 to 5 bases from the 5' end. The process for testing for $PrP^{Sc}$ comprises:

(a) obtaining a reagent mix comprising microspheres, fibrinogen, prothrombin, Factor Va, and Factor X, and buffer;

(b) incubating separately for at least 5-20 minutes at about 10° C. to about 37° C. a sample for testing, a bifunctional aptamer and RVV-X activator;

(c) adding the reagent mix; and (d) determining the presence of the infectious agent by observing clotting.

Preferably, the step of determining the presence of the infectious agent is determined by blood coagulation or by a spectrophotometer reading of an optical density (OD) at approximately 405 nm. Preferably, the reagent mix further comprises from about 500 nM to about 700 nM phospholipid vesicles (for example, a mixture of phosphatidylserine:phosphatidylcholine). Preferably, the amount of fibrinogen in the reagent mix is from about 150 nM fibrinogen to about 300 nM. Preferably, the amount of prothrombin in the reagent mix is from about 150 nM to about 300 nM. Preferably, the reagent mix further comprises polymer microspheres to aid in the visual determination of clotting. Most preferably, the polymer microspheres are made from polystyrene. Preferably, the method is conducted in a multiwell plate. Preferably, the buffer in the reaction mix is selected from the group consisting of phosphate buffer, PBS (phosphate buffered saline), IC buffer (imidazole-HCl, $CaCl_2$), Heparin BSA buffer (Tris-HCl, NaCl, EDTA, PEG600, BSA), HEPES, TAE, isocitrate and combinations thereof.

The present disclosure further provides a component for detecting the presence of an agent configured in a bifunctional allosteric aptamer comprising a first sequence component, and a second sequence component, wherein the first sequence component is a complement binding sequence component selected from the group consisting of SEQ ID NOs 1-89 and 92-96, each having a 5' end and a 3' end, wherein the second sequence component binds to an agent, and wherein the second sequence component sequence is inserted into the first sequence component from 1 to 5 bases from the 5' end.

DESCRIPTION OF THE FIGURES

FIGS. 9A-C show examples of EMSA for monoclonal RNA aptamer sequences binding to RVV-X. RNA species used for gel shift are SEQ ID NOS. 98, 103, and 90 for FIGS. 9A, 9B, and 9C, respectively. Lanes 1-12 include 0.25 fmol end-labeled RNA with varying concentrations of RVV-X or BSA negative control protein. From left to right [RVV-X] (+RNA): 0, 8.66 nM to 4.44 μM (11 concentrations total), BSA (6 pmol/9 microL) (+RNA). For FIGS. 9A and 9B, lane 13 contains 2.22 μM RVV-X only. Note in FIG. 9C, lane 13 includes carry-over from lane 12.

DETAILED DESCRIPTION

Figure 1:
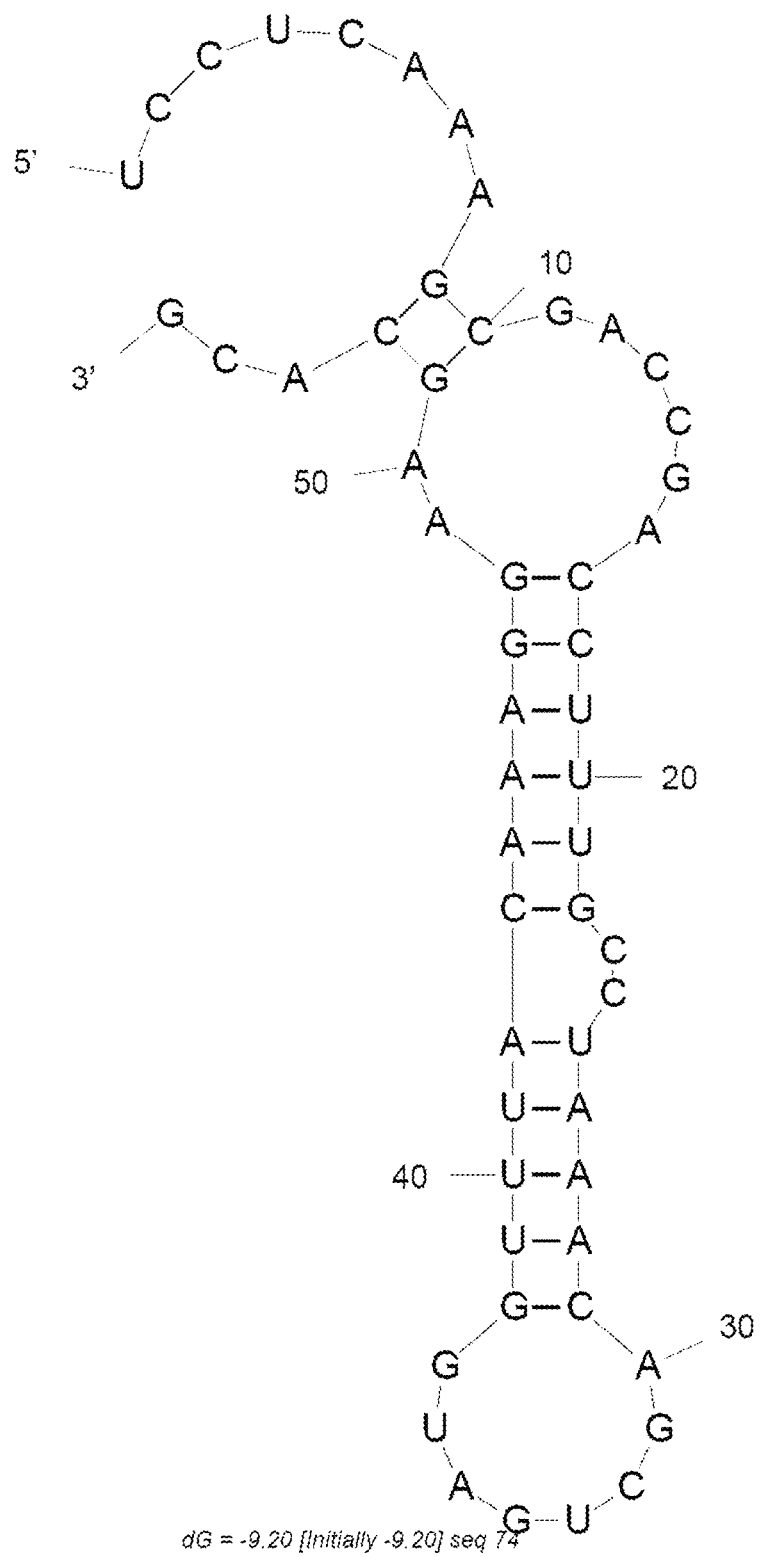
FIG. 1 shows a structural sequence of the first 55 bases to the complement cascade binding region (RVV-X Binding Region) of a preferred aptamer (SEQ ID NO. 74). This is also referred to as the first sequence component. This first sequence component of the preferred aptamer comprises two stems, a bulge, and two loop regions. The first stem region comprises bases 9-10 corresponding to bases 51-52. The second stem region comprises bases 17-29 and bases 38-48 and having a bulge (bases 22-25 and bases 42-43) contained therein. The first loop extends from bases 10-17 and 48-51 and the second loop is bases 29-38.
Figure 2:
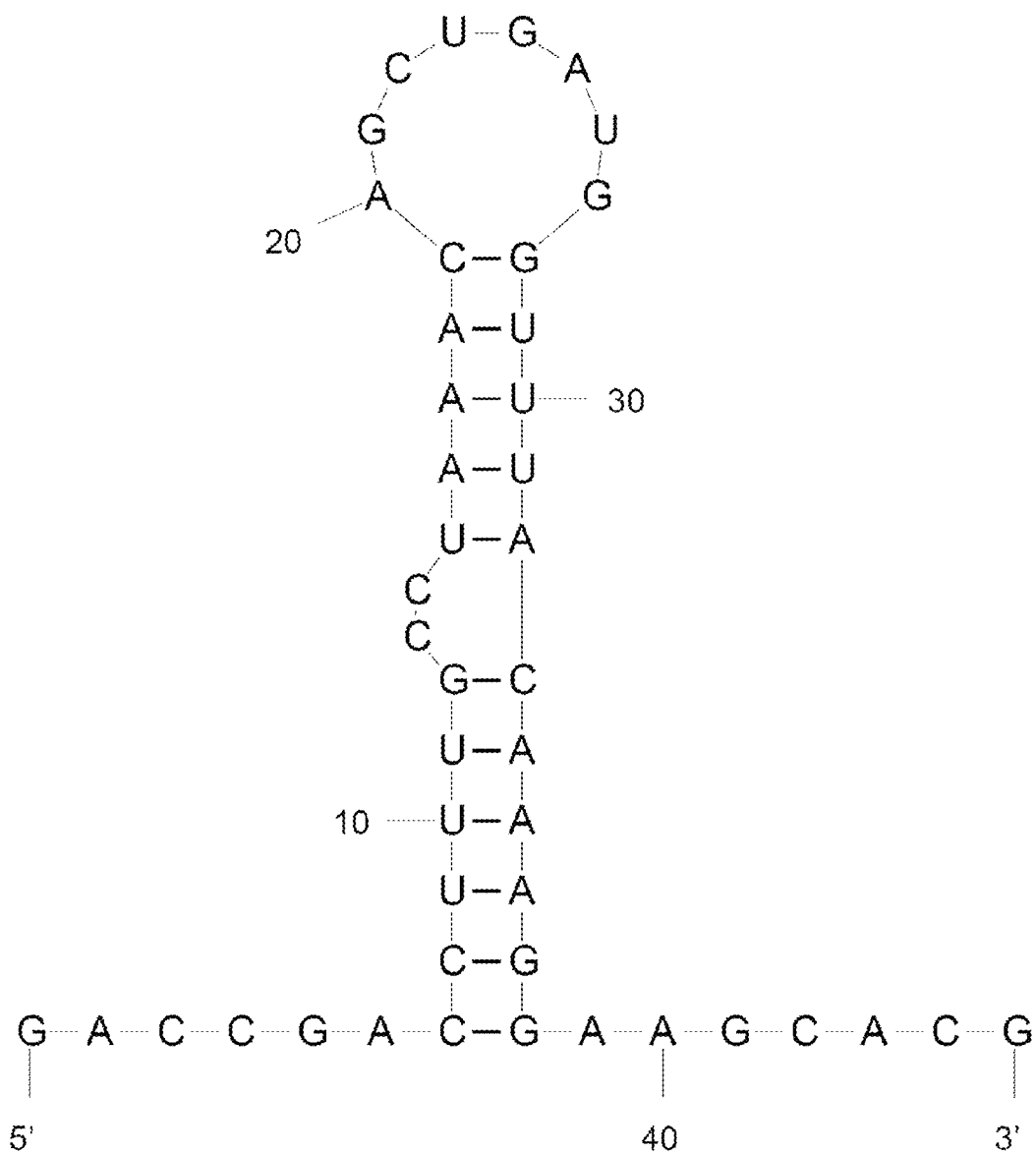
FIG. 2 shows a structural sequence of the 45 bases of the first sequence component of a preferred aptamer (SEQ ID NO. 97) comprising one stem, one bulge, and one loop region. The stem region comprises bases 7-19 and bases 28-38, having a bulge (bases 12-15 and bases 32-33) contained therein. The loop extends from bases 19-28.
Figure 3:
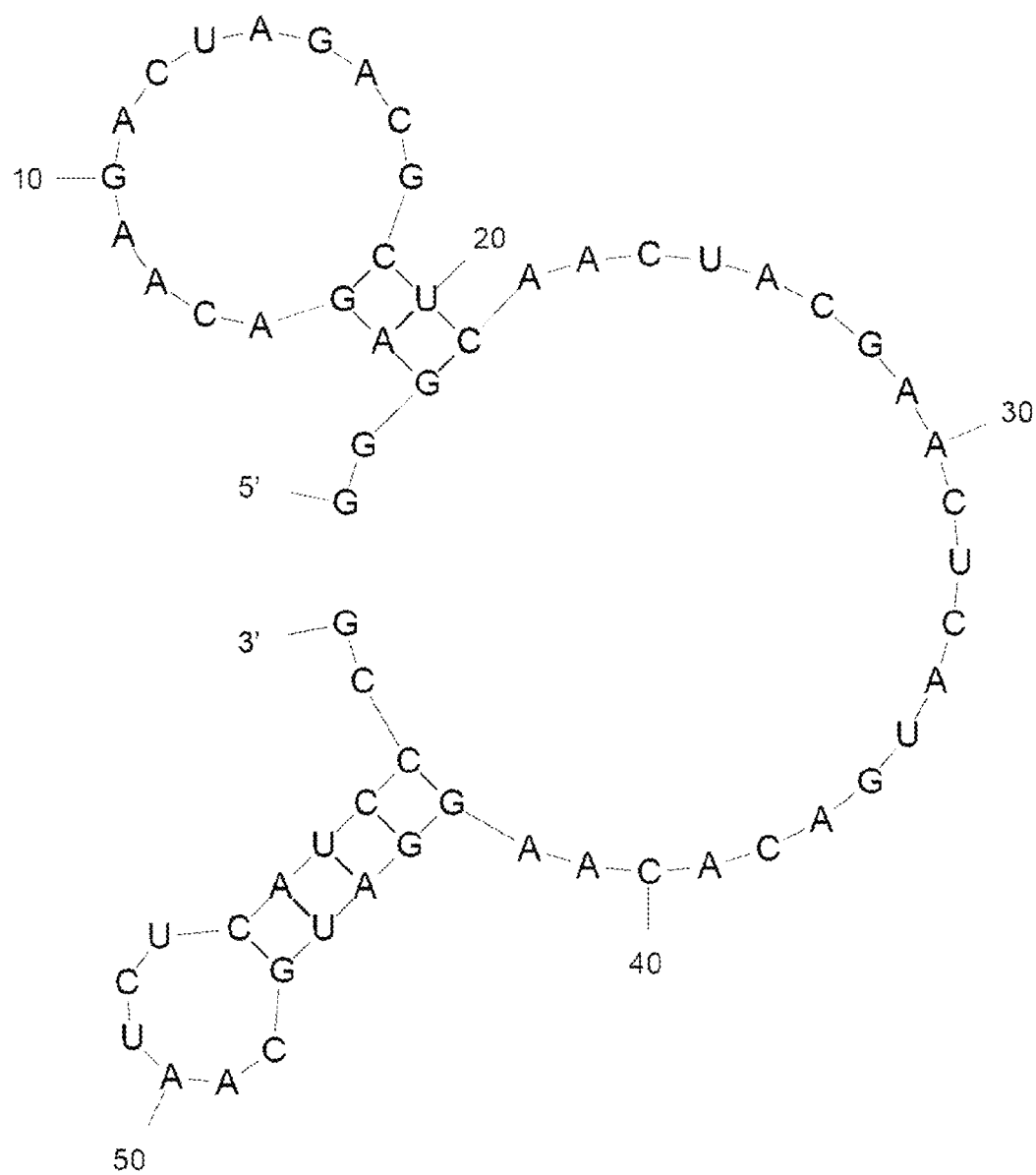
FIG. 3 shows the prion binding region ($PrP^{Sc}$ Binding Region) having 60 RNA bases of a preferred aptamer disclosed herein. This is also referred to as the second sequence component. This region of the preferred aptamer (SEQ ID NO. 90) comprises two loops and two short stems. The first loop is from bases 5-19 and the second loop is from bases 47-54. There is one stem from bases 3-5 corresponding to bases 19-21 and a second stem from bases 43-47 corresponding to bases 54-58.
Figure 4:
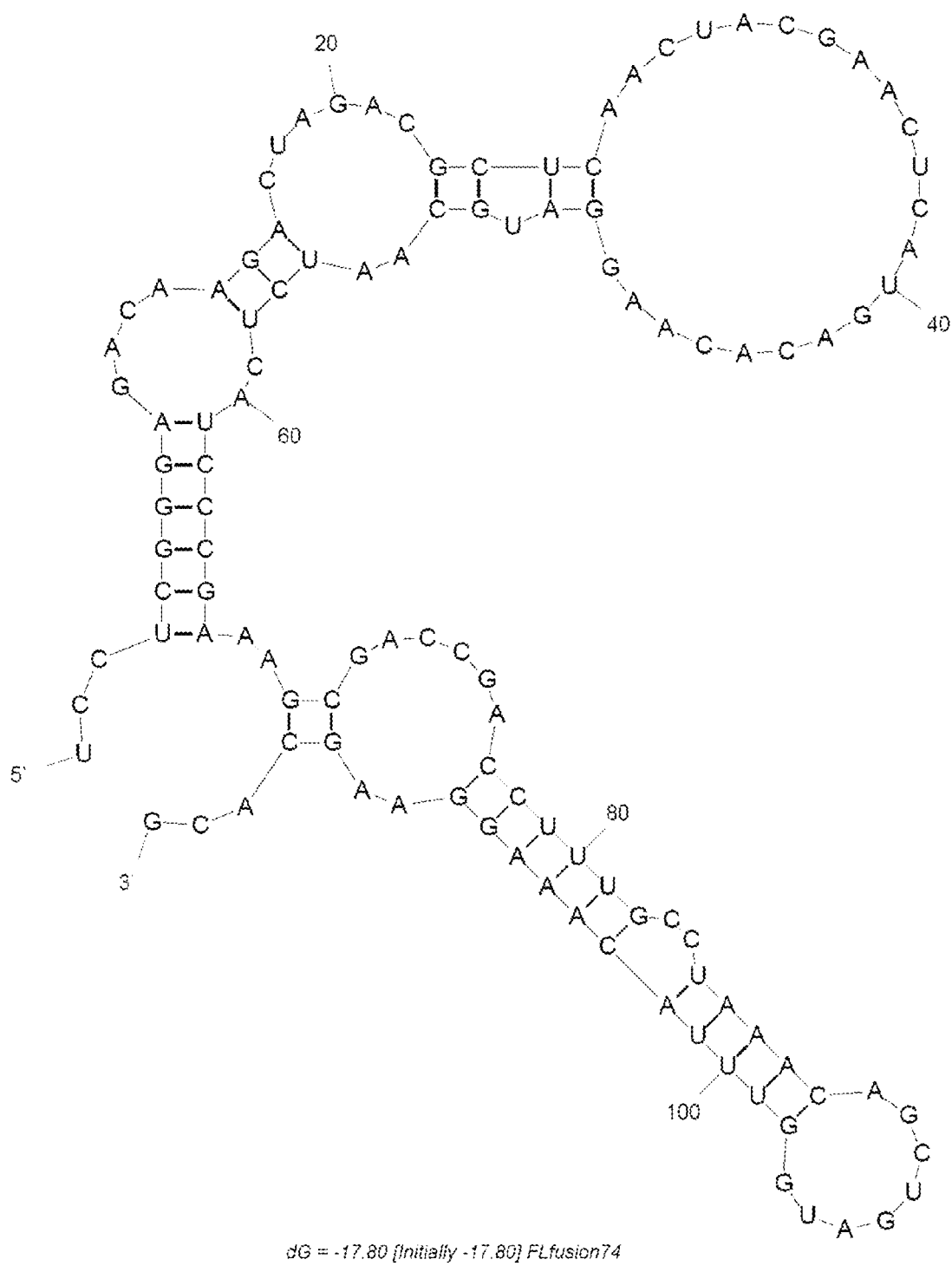
FIG. 4 shows a second preferred embodiment fully formed bifunctional aptamer (SEQ ID NO. 98) having both a prion binding region (second sequence component) and a complement cascade binding region (first sequence component) and having five main loops, two bulges, and five stem regions.

The present disclosure provides a bifunctional RNA aptamer-based competitive homogeneous detection system having a readout by the naked eye. This became possible by coupling an RNA aptamer with a biochemical signal amplification cascade, BCC-MS. The signal amplification cascade resulted in the formation of the precipitate of polystyrene microspheres bound to clotted fibrin. In a preferred embodiment, the aptamer contains a domain that binds to RVV-X, thus inhibiting BCC. There is another domain on the aptamer which binds to an effector molecule, reversing the effect of the first domain. The latter domain of the aptamer is the only variable part of the detection system. Therefore, adjusting the detection system to a new effector molecule will involve only one molecular component, an aptamer to the effector molecule. The disclosed bifunctional aptamer provides features that can insert a detection system into a platform for on-site testing. Therefore, the presently disclosed bifunctional aptamer provides a commercial advantage of being field-deployable/on-site, relatively rapid to minimize the quarantine time for tested animals, and relatively inexpensive because no sophisticated laboratory equipment is necessary and the bifunctional aptamers can be manufactured by standard commercial nucleic acid synthesis techniques.

In one embodiment, a disclosed RNA aptamer (e.g., SEQ ID NOs. 1-89) selectively binds an activated or inactivated form of the protease RVV-X. Preferably, the dissociation constant ranges from about 10 pM to about 100 nM. More preferably, the dissociation constant ranges from about 100 pM to about 100 nM, and can optionally comprise any value within the range, e.g. about 800 pM, about 900 pM, about 1 nM, about 2 nM, or about 5 nM.

TABLE 1

RNA Sequence Listing for first sequence component to RVV-X

RNA sequence of first component (SEQ ID NOs 1-89)

| | |
|---|---|
| UAGCGACAAGGCGACAAGCAAUGACACAUUAACAGACCCUGGUUAGUGAACGAA | SEQ ID NO. 1 |
| AAGGCGAGGUGCGACCCGCACGUGGCAUCUGAUAGCACAUGAAAAGGCACGUCA | SEQ ID NO. 2 |
| UCUUCCAACGACCAUGCGGCGACAAGCGACUACAAGAGGGUACCCACGGACAGCA | SEQ ID NO. 3 |
| UGGCGACGAGGCGGCAGGCAAUGACACAUUAGCAGACCCUGGUUAAUGAGCGAA | SEQ ID NO. 4 |
| UAGCGACAAGGCGACAAGCAAUGACACAUUAACGGACCCUGGUUAAUGAACGAA | SEQ ID NO. 5 |
| UGGCGGAUACUCUGCGAAGGGCGAACCCAACAUUUCGCACAGGACCGACUACUGCA | SEQ ID NO. 6 |
| UGGCGGAUACUCUGCGAAGGGCGAACCCAACAUUUCGCACAGAACCGACUACUGCA | SEQ ID NO. 7 |
| AAGCGACAAGGCGACAAGCAAUGACACAUUAACAGACCCUGGUUAAUGGACGAC | SEQ ID NO. 8 |
| AGGCGACAAGGCGACAAGCAAUGUCACAUUAACAGACCCUGGUUAAUGAACGAA | SEQ ID NO. 9 |
| UAGCGACAAGGCGACAGGCAAUGGUACAUUAACAGACCCUGGUUAAUGAACGAA | SEQ ID NO. 10 |
| UAGCGACAAGGCGACGAGCAACGACACAUUAACAGACCCCGGUUAAUGAACGAA | SEQ ID NO. 11 |
| UAGCGAGAAGGCGACAAGCAACGACACAUUAACAGACCCUGGUUAAUGGACGAA | SEQ ID NO. 12 |
| UAGCGCCGAGGCGACAGGCGACGACACAUUAACAGACCCUGGUUAAUGAGUGAA | SEQ ID NO. 13 |
| UAGCGGACACUCUGCGAAGGGCGAACCCAACAUUUCGCACGGAACCGACUACUACA | SEQ ID NO. 14 |
| UCCGAUCUUCAUACCCGCGACCGGCGACAUUGUGACCGCAAAACCGGACAACCCC | SEQ ID NO. 15 |
| UGGCGAUACUCUGCGAAGGGCGAACCCAACAUUUCGCACAGAACCGACUACUGCA | SEQ ID NO. 16 |
| AAGGCGAGGCGCGACCCGCACGUGACAUCCGAUACCACGUGAAAAGGCACGACA | SEQ ID NO. 17 |
| UAGCGACAAGGCGACAAGCAACGACACAUUAACAGACCCUGGUUAAUGAACGAA | SEQ ID NO. 18 |
| UAGCGACAAGGCGACAGGCAACGACGCAUUAACAGACCCUGGUUGAUGAACGAA | SEQ ID NO. 19 |
| UAGCGACAAGGCGACAGGCAAUGACACAUUAUAGACCCUGGUUAAUGAACGAA | SEQ ID NO. 20 |
| UAGCGACAAGGCGACGAGCAAUGGCACAUUAACAGACCCUGGUUAAAGAACGGG | SEQ ID NO. 21 |
| UAGCGACAAGGCGGCAAGCAACGACGCAUUAACAGACCCUGGUUAAUGAAUGAA | SEQ ID NO. 22 |
| UAGCGACGGUGCGACAAGCAAUGGCACAUUAACAGACCCUGGUUAAUGAACGAA | SEQ ID NO. 23 |
| UAGCGACUAGGCGACAAGCAAUGACACAUUAACAGACCCUGGUUAAUGAACGAA | SEQ ID NO. 24 |
| UAGGCGAGGCGCGACCCGCACGUGACAUCUGAUAGCACGUGAAAAGACACUACA | SEQ ID NO. 25 |
| UGAUUGGAAUUCUUGGGGCCGAGCGACCCGGCCGUGUAUGAGACAAGAUUACUCC | SEQ ID NO. 26 |
| UGGAGUUUGAUUGCGACCGGGGCGACACCCACAAAGGCGACAAAAUCAUUCACAC | SEQ ID NO. 27 |
| UGGCGACAAGGCGACAAGCAAUGACACAUUAACAGACCCUGGUUAAUGAACGUA | SEQ ID NO. 28 |
| UGGCGGAUACUCUGCGAAGGGCGAACCCAACAUUUCGCACAGAACCGGCUACUCCA | SEQ ID NO. 29 |
| UGGCGGCUACUCUGCGAAGGGCGAACCCAACAUUUCGCACAGAACCGACUACUGCA | SEQ ID NO. 30 |
| UUGCUCGUACCCUGGGAGCAAAGACCUGAUCAGACCCAACAGAUCUAACAAGCA | SEQ ID NO. 31 |
| AAGCGACGAGGCGACAAGCAAUGACACAUUAACAGACCCUGGUUAAUGGACGAA | SEQ ID NO. 32 |
| ACGGUGGCGCGGGCGGACCCAAAAUGACGCCACAAAGAAGGCAACACAGAAAACA | SEQ ID NO. 33 |
| ACGGUGGCGCGGGCGGACCCAAAAUGACGCCACAAAGAAGGCAACACAGAAACA | SEQ ID NO. 34 |
| CAGCGACAAGGCGACAAGCAAUAGACACGUUAACAGACACUGGUUAAUGAACGA | SEQ ID NO. 35 |
| CAGCGACGAGGCGACAGGCAACGACACAUUAACAGACCCCGGUUAAUGAGCGAA | SEQ ID NO. 36 |
| CUGCGACAAGGCGACAAGCAACGACACAUUAACAGGCCCUGGUUAAUGAACGGA | SEQ ID NO. 37 |
| GACAGUAUUUGCGGGGCAAGGGCGCGACAACAAACACAAGUACAGAAAAGGCUA | SEQ ID NO. 38 |

TABLE 1-continued

RNA Sequence Listing for first sequence component to RVV-X

| Sequence | SEQ ID NO. |
|---|---|
| GAGCGACGAGGCGUCAAGCAAUGACACAUUAACAGACCCUGGCUAAUGAAUGAA | SEQ ID NO. 39 |
| GCUGAGGGCGGCGACCAGUACAUGCAGCGACAAAUGUACACACAAGCGACGAAAA | SEQ ID NO. 40 |
| UACCUUAUUCCGCCCCCGCUGCCCUGGACGUGGAGACUCUGAAACUCCAGCUAU | SEQ ID NO. 41 |
| UAGCAACAAGGCGACAGGCAAUGACACAUUAACAGAACCUGGUUAAAGAACGAA | SEQ ID NO. 42 |
| UAGCAACAAGGCGACUAGCAACGACACAUUAACAGGCCCUGGUUAAUGGACGAA | SEQ ID NO. 43 |
| UAGCAACAAGGCGAUAAGCAAUGGCACAUUAACUGGCCCUGGUUAAUGAACGAA | SEQ ID NO. 44 |
| UAGCGACAAGGCGACAAAGCAAUGACACAUUAACGGACCCUGGUUAAUGAACGAA | SEQ ID NO. 45 |
| UAGCGACAAGGCGACAAGCAACGACACAUUAACAGACCCUGGCUAAUGACGAAA | SEQ ID NO. 46 |
| UAGCGACAAGGCGACAAGCAACGACACAUUAACAGACCCUGUUAAUGAACGAAA | SEQ ID NO. 47 |
| UAGCGACAAGGCGACAAGCAACGACACAUUAACGGACCCUGGUUAAUGGACGAA | SEQ ID NO. 48 |
| UAGCGACAAGGCGACAAGCAACGACACGUUAACAGACCCUGGUUAAUGAACGAA | SEQ ID NO. 49 |
| UAGCGACAAGGCGACAAGCAAUGACACAUUAACAGACCCUGGUUAAUGAACGAA | SEQ ID NO. 50 |
| UAGCGACAAGGCGACAAGCAAUGACACAUUAACAGACCCUGGUUAAUGAACGAG | SEQ ID NO. 51 |
| UAGCGACAAGGCGACAAGCAAUGACACAUUAAUAGACCCUGGUUAAUGGACGAA | SEQ ID NO. 52 |
| UAGCGACAAGGCGACAAGCAAUGACCCAUUAACAGGCCCUGGUUAAUCAACGAA | SEQ ID NO. 53 |
| UAGCGACAAGGCGACAAGCAAUGGCACAUUAACAGACCCUGGUUAACGAACGAA | SEQ ID NO. 54 |
| UAGCGACAAGGCGACAAGCAAUGGCACAUUGACAGACCCUGGUUAAUGAGAGAA | SEQ ID NO. 55 |
| UAGCGACAAGGCGACAAGCGAUGACACAUUAACAGGCCCUGGUUAAUGAAUGAA | SEQ ID NO. 56 |
| UAGCGACAAGGCGACAGGCAAUGACACAUUAAAUAGACCCUGGUUAAUGAACGAA | SEQ ID NO. 57 |
| UAGCGACAAGGCGACAGGCAAUGACACAUUAACAGACCCUGGUUAAUGAACGAA | SEQ ID NO. 58 |
| UAGCGACAAGGCGACAGGCAAUGACACAUUAACAGACCCUGGUUAAUGAAUGAA | SEQ ID NO. 59 |
| UAGCGACAAGGCGACAGGCAAUGACACAUUAACAGGCCCUGGUUAAUGAACGAA | SEQ ID NO. 60 |
| UAGCGACAAGGCGACAGGCAAUGACACAUUAGCGGACCCUGGUUAAUGAACGAA | SEQ ID NO. 61 |
| UAGCGACAAGGCGACAGGCAAUGCCUCAUUAGCAGACCCUGGUUAAUGAACAAA | SEQ ID NO. 62 |
| UAGCGACAAGGCGACGAGCAAUGGCACAUUAACAGACCCUGGUUAAUGAACGAAA | SEQ ID NO. 63 |
| UAGCGACAAGGCGACGGGCAAUGACCCAUUAACAGACCCUGGUUAAUGAACGAA | SEQ ID NO. 64 |
| UAGCGACAAGGCGGCAGGCAAUAACACAUUAACAGACCCCGGUUAAUGAACGAA | SEQ ID NO. 65 |
| UAGCGACAAGGCGGCGAGCAAUGACACAUUAACGGACCCUGGUUAAUGAACAAA | SEQ ID NO. 66 |
| UAGCGACUAGGCGACAAGCAAUGACACAUUAACAGACCCUGGUUAAAUCGAACGAA | SEQ ID NO. 67 |
| UAGCGACUAGGCGACGGGCAAUGACGCAUUAACAGGCCCUGGUUAAUGAACAGA | SEQ ID NO. 68 |
| UAGGCGAGGCGCGACCCGCGCGGGACAUCUGAUAGCACGUGAAAAUGGCACAACG | SEQ ID NO. 69 |
| UAGGCGAGGCGCGACCCGCGCGUGACAUCUGAUAGCACGUGAAAAGGCACGACA | SEQ ID NO. 70 |
| UAGGCGAGGCGGGACCCGCACGUGACAUCUGAUAGCACGUGAAAAGGCACGACAA | SEQ ID NO. 71 |
| UCAAUAAAUGGCAGACCUGAUGCUGCGGGCGUAAGGCAUAGCGACCAACAUUCU | SEQ ID NO. 72 |
| UCCCCGAUACUGCGACCAACAGAUUACCAGGGCGAACAGCGACCGAGCAACAAUG | SEQ ID NO. 73 |
| UCCUCAAAGCGACCGACCUUUGCCUAAACAGCUGAUGGUUUACAAAGGAAGCACG | SEQ ID NO. 74 |
| UCCUUCCCCAAUGCGACACCCCAGCAAGGCGACAGCUGGCCAGGCGACAAACAAAA | SEQ ID NO. 75 |
| UCGCGACAAGGCGACGAGCAAUGGCACAUUAACAGACCCUGGUUAAUGAACGAA | SEQ ID NO. 76 |
| UCUGAGGGCGGCGGCCAGUACAUGCAGCGACAAAAUGUACACACAAGCGACAAAA | SEQ ID NO. 77 |

TABLE 1-continued

| RNA Sequence Listing for first sequence component to RVV-X | |
|---|---|
| UCUGGCGAGGGCGGCUAGGGGACACAGCGUAGUCUGAUGACGCAGAGCAAUCUAA | SEQ ID NO. 78 |
| UGGCGAAGACCCGAACACCCUGAGCUGUUUAAAGGCGACGACGCAGCGACGAGCC | SEQ ID NO. 79 |
| UGGCGAAGACCCGAUCACCCUGAGCUGUUUAAAGGCGACGACGCAGCGACGAGCC | SEQ ID NO. 80 |
| UGGCGACAAGGCGACAAAGCAAUGACACAUUAACAGACCCUGGUUAAUGAACGUA | SEQ ID NO. 81 |
| UGGCGACAAGGCGACAGGCAAUGAACACAUUAACGGACCCUGGUUAAUGAACGAA | SEQ ID NO. 82 |
| UGGCGACAAGGCGACAGGCAAUGACACAUUAACGGACCCUGGUUAAUGAACGAA | SEQ ID NO. 83 |
| UGGCGGAUACGCUGCGAAGGGCGAACCCAACAUUUCGCACAGAGCCGACUACUGCC | SEQ ID NO. 84 |
| UGGCGGAUACUCUGCGAAGGGCGAACACAACAUUUCGCACAGAACCGACUACUGCA | SEQ ID NO. 85 |
| UGGCGGAUACUCUGCGAAGGGCGAACCCAACAUCUCGCACAGAACCGACUACUGCG | SEQ ID NO. 86 |
| UGGCGGAUACUCUGCGAAGGGCGAACCCAACGUUUCGCACAGAACCGACUACUGCG | SEQ ID NO. 87 |
| UUGCUCAUACCCUGAGAGCAAAGAUCUGAUCAGACCCAACAGAUCUAGCAAGCAU | SEQ ID NO. 88 |
| UUGGUGGCGCGGGCGAACCCAAAAUGACGCCACAAAGAAGACAAUACAGGAAGCA | SEQ ID NO. 89 |
| RNA Sequence of second component | |
| GGGAGACAAGACUAGACGCUCAACUACGAACUCAUGACACAAGGAUGCAAUCUCAUCCCG | SEQ ID NO. 90 |
| UUUACCGUAAGGCCUGUCUUCGUUUGACAGCGGCUUGUUGACCCUCACACUUUGUACCUG CUGCCAA | SEQ ID NO. 91 |

RNA was synthesized by in vitro transcription using a Durascribe Transcription kit (Epicentre Biotechnologies) according to manufacturer instructions. RNA molecules were resuspended in IC buffer (50 mM imidazole-HCl, 3 mM $CaCl_2$, pH 7.8), heated to 95° C. and cooled slowly over the course of 2 hrs to room temp, then moved to ice to achieve final secondary structure for use in a diagnostic assay. In a preferred embodiment, each of the pyrimidine bases in sequences SEQ ID NOS. 1-108 are 2' fluoro-modified. (2'-F-C, U-RNA).

The disclosed aptamer sequences are further modified. SEQ ID NO 97 recognizes RVV-X—involved in detection readout. SEQ ID NO 90 recognizes $PrP^{Sc}$. For example, by specifically modifying the regions provided in SEQ ID NO 97 and SEQ ID NO 90 herein. Sequence modification separately modifies SEQ ID NO. 97 while holding the region of SEQ ID NO. 104 steady. Alternatively, one can separately modify SEQ ID NO. 90 while holding the region of SEQ ID NO. 97 steady. Alternatively, several bases are removed to achieve minimal aptamer binding both RVV-X and $PrP^{Sc}$ or insertion of bases, such as removal of: SEQ ID NO. 106 in SEQ ID NO. 97. Further and alternatively still one can remove bases at the 3' or 5' ends of SEQ ID NO. 106, or SEQ ID NO. 90, or SEQ ID NO. 97 either singly or up to 10 consecutive bases. Further and alternatively still, one can remove bases within SEQ ID NO. 106, or SEQ ID NO. 90, or SEQ ID NO. 97 either singly or up to 60 consecutive bases (and sets of 10). Or within the SEQ ID NO. 103 containing secondary structure base-pairing, removal of base pairs entails removal of bases at a 5'end and removal of the 3' complementary base to which it base-pairs, including, for example, insertion of: bases at 3' or 5' ends of SEQ ID NO. 106, or SEQ ID NO. 90, or SEQ ID NO. 104 either singly or up to 10 consecutive bases. The present disclosure further provides for insertion of bases within SEQ ID NO. 106, or SEQ ID NO. 90, or SEQ ID NO. 97 either singly or up to 60 consecutive bases. Within SEQ ID NO. 103 containing secondary structure base-pairing, removal of base pairs entails removal of bases at a 5'end and removal of the 3' complementary base to which it base-pairs. Table 4 lists the truncations of SEQ ID 74 (from Table 3) as fusions with SEQ ID NO. 90 as the second sequence component, constructed in the same manner listed above. Alternately, SEQ ID NO. 91 may be used in place of SEQ ID NO. 90.

Example 1

This example illustrates reaction times of an in vitro blood coagulation cascade. Time points were taken at 3 minute intervals after 20 seconds of plate shaking with photographic documentation using a Canon EOS XSI (50 mm fixed lens, ISO 100, (f-stop) f/11.0, 15 second exposure.) Serial dilutions of RVV-X Snake Venom protease activator (Haematologic Technologies, VT) were prepared in IC buffer (50 mM imidazole-HCl, 3 mM $CaCl_2$, pH 7.8); the amount of activator listed on the Y-axis is in a 1 µL sample volume. 95 µL reaction buffer is added to 1 µL RVV-X, and shaken initially for 30 seconds. Then, the reaction was monitored over 90 minutes at room temperature and various time points were photographed. Control was either IC Buffer only (1 µL, top lane) or 100 fmol non-acetylated BSA (Sigma Aldrich) (bottom row).

Figure 6:
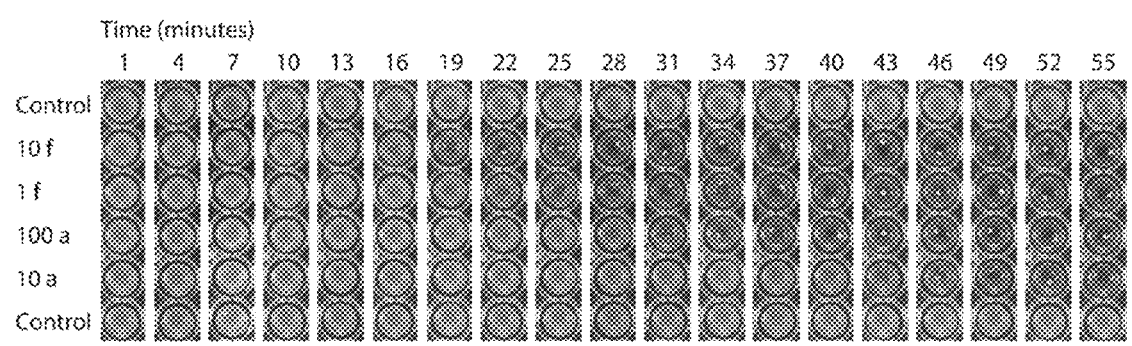
FIG. 6 shows a microwell plate with pictures and time points of reaction progression as described in Example 1 herein.
Figure 7:
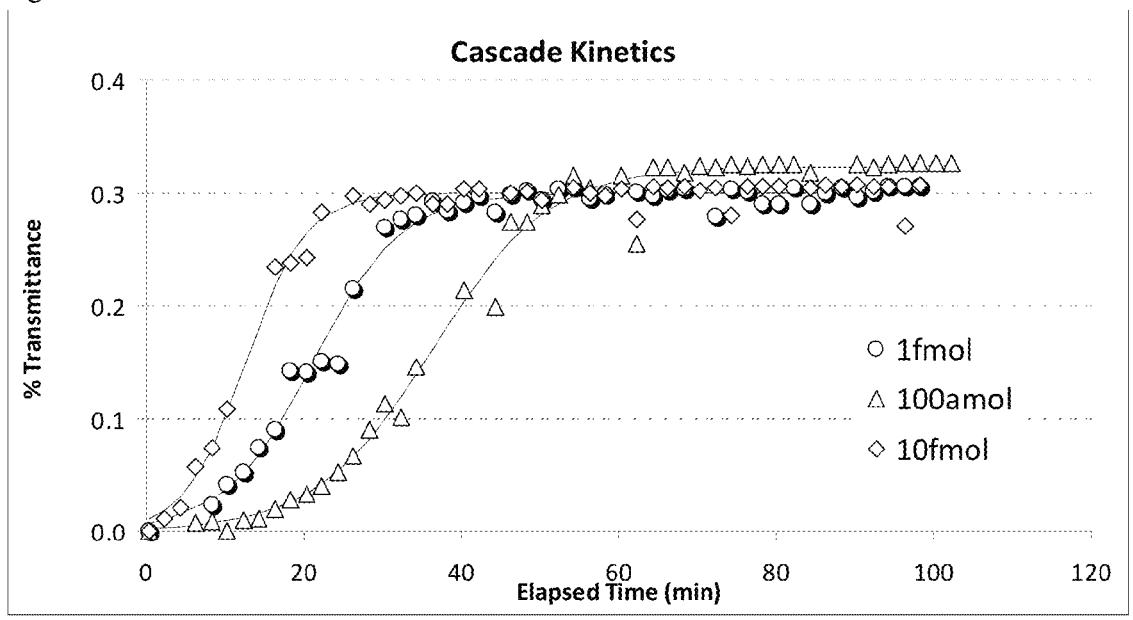
FIG. 7 shows the kinetics of the cascade described in Example 1. Percent transmittance through the in vitro cascade reaction mix was plotted as a function of time for several concentrations of RVV-X activator. Varying amounts of RVV-X (10 fmol, 1 fmol, 100 amol) were added to 100 μL of reaction mix and absorbance was monitored over time. The data was then transformed to % transmittance and plotted vs. $t_{1/2}$, which were calculated: 12.6 min (10f), 21.2 min (1f), 36.3 min (100a).
Figure 8:
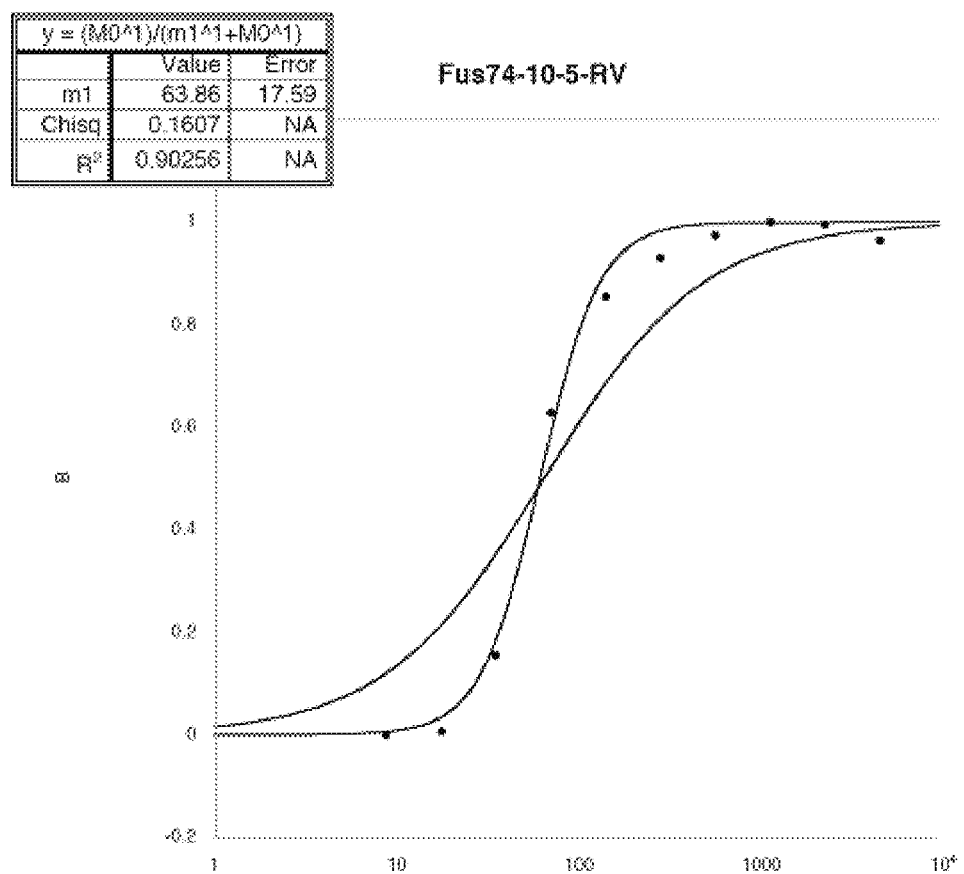
FIG. 8 shows a Kaleidagraph illustration of a $K_{d(app)}$ calculation for the aptamer SEQ ID NO. 103 to RVV-X; the gel shift is in FIG. 9B. Data were obtained from densitometry scanning using a BioRad FX Scanner and quantified with Quantity One software. Normalized data were plotted in Kaleidagraph and values for $K_d$ (m1) and the Hill coefficient (m2) were calculated: $K_d$ (m1 in legend)=63.86 nM, and Hill coefficient (m2)=1.0 (no cooperativity).

In FIG. 6, the reaction times for initial phase transition of the BCC reaction upon addition of RVV-X were: 10 fmol, 13 min; 1 fmol, 16 min; 100 amol, 22-25 minutes; 10 amol, 37 minutes. The negative control (no RVV-X) did not react within the observed time frame. FIG. 7 includes data taken using a microplate reader at 405 nm and graphed in Microsoft Excel.

Table 2 shows the data from a BCC reaction that was prepared according to Example 1. Data were taken at two or three minute time points on a Synergy H1 Hybrid Reader (BioTek) using Gen5 data analysis software. Time points ($t_{1/2}$) were calculated using Excel Solver and filtered to remove outliers. Assay CV was <5% (little noise).

TABLE 2

Average $t_{1/2}$ of BCC reaction (filtered data).

| RVV-X (per 100 μL reaction) | Avg $t_{1/2}$ (min) | St dev | CV (%) | N (sample size) |
|---|---|---|---|---|
| 10 f | 12.40 | 0.26 | 2.1 | 3 |
|  | 15.17 | 0.57 | 3.7 | 3 |
| 1f | 20.80 | 0.42 | 2.0 | 2 |
|  | 28.47 | 1.20 | 4.2 | 3 |
| 100a | 36.57 | 0.74 | 2.0 | 3 |
|  | 42.90 | 0.14 | 0.3 | 2 | electrophoresed on a 7% non-denaturing polyacrylamide gel in 0.5×TBE for 40 minutes at 120V. The gel was then dried and exposed to film for 2 hrs or overnight. Film was developed and scanned. Bands were quantified by densitometry and $K_d$ calculated by fitting data to a non-linear regression curve using a One Site-Specific Binding with Hill Slope model with Kaleidagraph. BSA (660 nM) and Human alpha-Thrombin (alpha-Thr) (4.4 μM, Haematologic Technologies) were used as negative controls. In this example, aptamer sequences Flfus74 (SEQ ID NO. 98) and Fus74_10_5 (SEQ ID NO. 103) were titrated against varying concentrations of RVV-X for $K_d$ assessment (FIGS. 9A-B). The $K_d$s were measured as 60 and 63 nM, respectively. $K_d$ values for selected monoclonals are in Tables 3-5. Gel-shift of B-end (SEQ ID NO. 90) to the control protein alpha-Thr is illustrated in FIG. 9C. The $K_d$ for this aptamer-protein set is 4224±483.6 nM. The measured $K_d$s of SEQ ID NO. 90 to RVV-X and PrP were 170.2±2.9 nM and 44.3±34.0 nM, respectively.

TABLE 3

$K_d$ determinations of select RVV-X first part sequences. Binding kinetics to RVV-X.

| Sequence | $K_d$ (nM) |
|---|---|
| UAGCGACAAGGCGACAAGCAAUGACACAUUAACAGACCCUGGUUAGUGAAC GAA SEQ ID NO. 1 | 30 |
| AAGGCGAGGUGCGACCCGCACGUGGCAUCUGAUAGCACAUGAAAAGGCACG UCA SEQ ID NO. 2 | 23.04 |
| UCUUCCAACGACCAUGCGGCGACAAGCGACUACAAGAGGGUACCCACGGAC AGCA SEQ ID NO. 3 | 94.7 |
| UGGCGACGAGGCGGCAGGCAAUGACACAUUAGCAGACCCUGGUUAAUGAGC GAA SEQ ID NO. 4 | 158.4 |
| UGGCGGAUACUCUGCGAAGGGCGAACCCAACAUUUCGCACAGGACCGACUA CUGCA SEQ ID NO. 6 | 19 |
| UCCUCAAAGCGACCGACCUUUGCCUAAACAGCUGAUGGUUUACAAAGGAAG CACG SEQ ID NO. 74 | 75 |
| GGAGG CCAAC UAAUA ACGCC AGAAC UAUAG GAAUC CCAUG AAGCG AGCGA GAAUU SEQ ID NO. 107 | 131 ± 19.7 |

A "Scrambled" sequence (SEQ ID NO. 107) is a randomized sequence of SEQ ID NO. 1 and was used as a negative control for the following studies.

Example 2

This example illustrates how $K_d$ values of monoclonal aptamers to RVV-X are determined. Electrophoretic mobility (gel) shift assays (EMSA) were performed on the RVV-X aptamer candidates (Tables 3-5) to measure $K_d$ values. Approximately 0.25 fmol $^{32}$P-end-labeled RNA was incubated with varying concentrations of RVV-X (0 nM and 8.66 nM-4.44 μM, 11 concentrations total) in a 9 μL total reaction volume for 1 hr at room temperature. Samples were mixed with 1.5 μL 6× glycerol loading buffer (Affymetrix) and Example 3

This example provides a series of bifunctional fusion aptamers of the present disclosure using SEQ ID NO. 74 as the first sequence component.

Table 4 below lists truncations of SEQ ID NO. 74. The truncated sequences for the first sequence component, SEQ ID NO. 74, are the fusion SEQ ID NOs 93-96. The species are labeled according to the region from which bases are truncated: "5 from 3'" means 5 bases were removed from the 3' end (in this list, from SEQ ID. NO. 74).

TABLE 4

Truncations of SEQ ID NO. 74 from RNA aptamer selection to RVV-X.

| Species | Size (nt) | $K_d$ (nM) | Sequence |
|---|---|---|---|
| 74 alone | 55 | 75 | UCCUCAAAGCGACCGACCUUUGCCUAAACAGCUGAUGGUUUA CAAAGGAAGCACG SEQ ID NO. 74 |
| 5 from 3' | 50 | 351.7 ± 48.4 | UCCUCAAAGCGACCGACCUUUGCCUAAACAGCUGAUGGUUUA CAAAGGAA SEQ ID NO. 92 |

TABLE 4-continued

Truncations of SEQ ID NO. 74 from RNA aptamer selection to RVV-X.

| Species | Size (nt) | K$_d$ (nM) | Sequence |
|---|---|---|---|
| 5 from 5' | 50 | 374 ± 12.7 | AAAGCGACCGACCUUUGCCUAAACAGCUGAUGGUUUACAAAG GAAGCACG SEQ ID NO. 93 |
| 5 from both | 45 | 426 ± 261.6 | AAAGCGACCGACCUUUGCCUAAACAGCUGAUGGUUUACAAAG GAA SEQ ID NO. 94 |
| 10 from 3' | 45 | 301.2 ± 33.6 | UCCUCAAAGCGACCGACCUUUGCCUAAACAGCUGAUGGUUUA CAA SEQ ID NO. 95 |
| 10 from 5' | 45 | 250 | GACCGACCUUUGCCUAAACAGCUGAUGGUUUACAAAGGAAGC ACG SEQ ID NO. 96 |

Table 5 includes the list of bifunctional fusion aptamers for monoclonal aptamer using SEQ ID NO. 74 as the first sequence component and SEQ ID NO. 90 as the second sequence component to form bifunctional fusion aptamers. These are labeled to describe the components of the aptamer: "Fus74_5_3" indicates the first sequence component is aptamer sequence 93 (SEQ ID NO. 93) and the second sequence component for all listed fusion aptamers in Table 5 is SEQ ID NO. 90. The construction of these fusion aptamers is described in Example 5.

Example 4

This example illustrates various second sequence components that can be used to form bifunctional aptamers that can measure PrP$^{Sc}$.

TABLE 6

Fusion aptamers of Table 3 first part sequences.

SEQ ID NO. 96 (45-mer):

5' GACCGACCUUUGCCUAAACAGCUGAUGGUUUACAAAGGAAGCACG 3'

TABLE 5

| SEQ ID NO | Fusion apt (seq 74) | Size (nt) | Sequence |
|---|---|---|---|
| 97 | Full Length | 115 | UCCUCGGGAGACAAGACUAGACGCUCAACUACGAACUCA UGACACAAGGAUGCAAUCUCAUCCCGAAAGCGACCGACC UUUGCCUAAACAGCUGAUGGUUUACAAAGGAAGCACG SEQ ID NO. 97 |
| 98 | 5 from 3' end | 110 | UCCUCGGGAGACAAGACUAGACGCUCAACUACGAACUCA UGACACAAGGAUGCAAUCUCAUCCCGAAAGCGACCGACC UUUGCCUAAACAGCUGAUGGUUUACAAAGGAA SEQ ID NO. 98 |
| 99 | 5 from 5' end | 110 | AAAGCGGGAGACAAGACUAGACGCUCAACUACGAACUCA UGACACAAGGAUGCAAUCUCAUCCCGGACCGACCUUUGC CUAAACAGCUGAUGGUUUACAAAGGAAGCACG SEQ ID NO. 99 |
| 100 | 5 from both ends | 105 | AAAGCGGGAGACAAGACUAGACGCUCAACUACGAACUCA UGACACAAGGAUGCAAUCUCAUCCCGGACCGACCUUUGC CUAAACAGCUGAUGGUUUACAAAGGAA SEQ ID NO. 100 |
| 101 | 10 from 3' end | 105 | UCCUCGGGAGACAAGACUAGACGCUCAACUACGAACUCA UGACACAAGGAUGCAAUCUCAUCCCGAAAGCGACCGACC UUUGCCUAAACAGCUGAUGGUUUACAA SEQ ID NO. 101 |
| 102 | 10 from 5' end | 105 | GACCGGGGAGACAAGACUAGACGCUCAACUACGAACUCA UGACACAAGGAUGCAAUCUCAUCCCGACCUUUGCCUAAA CAGCUGAUGGUUUACAAAGGAAGCACG SEQ ID NO. 102 |
| 90 | Second sequence component-BSE | 59 | GGGAGACAAGACUAGACGCUCAACUACGAACUCAUGACA CAAGGAUGCAAUCUCAUCCC SEQ ID NO. 90 |

TABLE 6-continued

Fusion aptamers of Table 3 first part sequences.

SEQ ID NO. 103 (40-mer):

5' ACCUUUGCCUAAACAGCUGAUGGUUUACAAAGGAAGCACG 3'
It should be noted that SEQ ID NO. 103 is
SEQ ID NO. 96 with the removal of five bases
from the 5' end.

SEQ ID NO. 90 (60-mer):

5' GGGAGACAAGACUAGACGCUCAACUACGAACUCAUGACACAAGGAU
GCAAUCUCAUCCCG 3'

SEQ ID NO. 103 (105-mer):

5' GACCGGGGAGACAAGACUAGACGCUCAACUACGAACUCAUGACACAA
GGAUGCAAUCUCAUCCCGACCUUUGCCUAAACAGCUGAUGGUUUACAAAG
GAAGCACG 3'

SEQ ID NO. 104 (105-mer):

5' GGGAGACAAGACUAGACGCUCAACUACGAACUCAUGACACAAGGAUG
CAAUCUCAUCCCG GACCGACCUUUGCCUAAACAGCUGAUGGUUUACAAA
GGAAGCACG 3'

TABLE 6-continued

Fusion aptamers of Table 3 first part sequences.

(5-MER):

5' GACCG 3'

SEQ ID NO. 105 (105-MER):

5' GACCGACCUUUGCCUAAACAGCUGAUGGUUUACAAAGGAAGCACG
GGGAGACAAGACUAGACGCUCAACUACGAACUCAUGACACAAGGAUGC
AAUCUCAUCCCG 3'

Example 5

Figure 5:
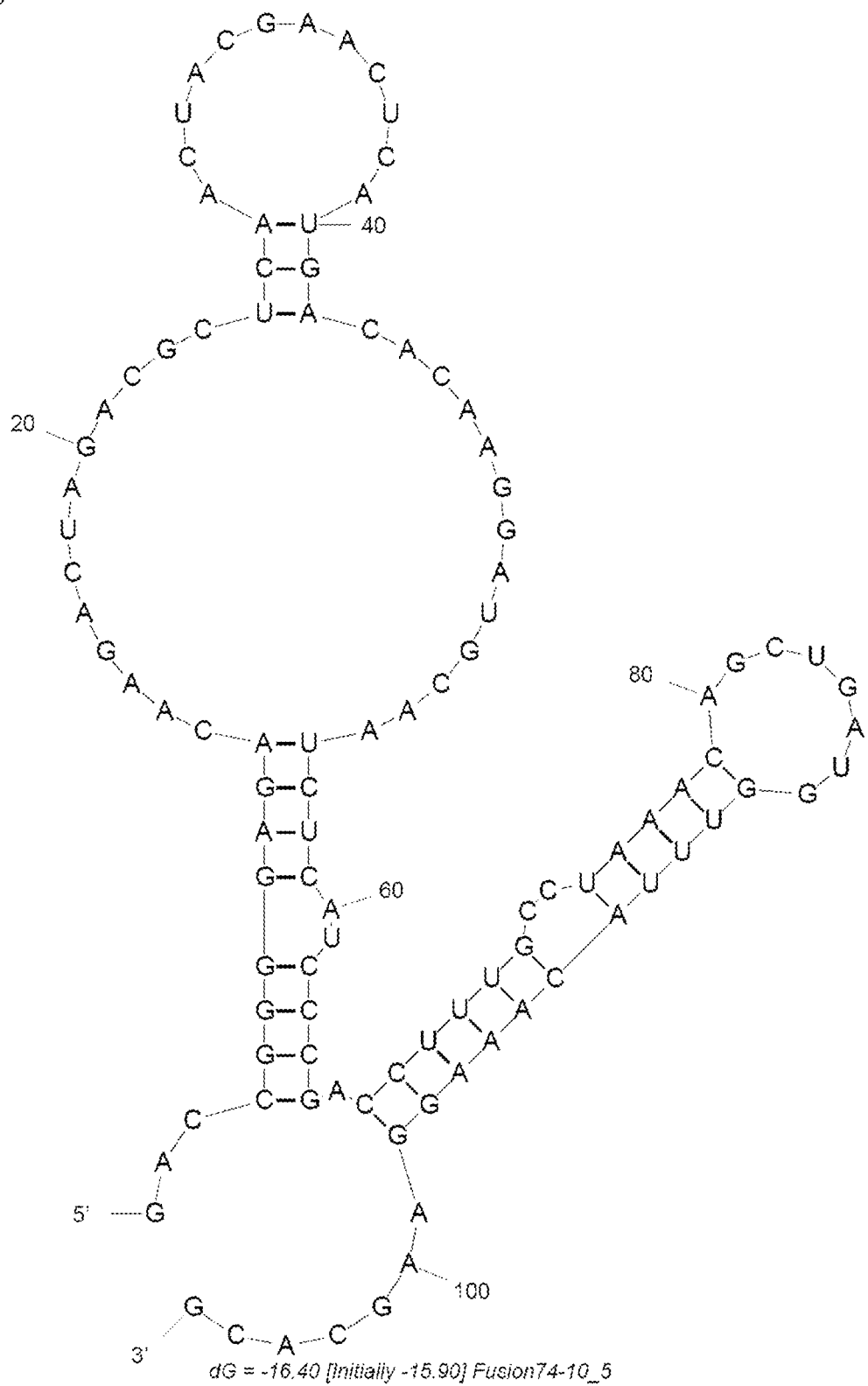
FIG. 5 shows a third preferred embodiment fully formed aptamer (SEQ ID NO. 103) having both a prion binding region (second sequence component) and a complement cascade binding region (first sequence component) and having three main loops, two bulges, and three stem regions.

The aptamer shown in FIG. 5 (SEQ ID NO. 103) was constructed by:
1) Adding SEQ ID NO. 90 to the 3' end of SEQ ID NO 105.
2) Inserting SEQ ID NO. 103 to the 3' end of SEQ ID NO. 90.
   The bifunctional fused aptamer of (SEQ ID NO. 104) was constructed by:
1) Adding SEQ ID NO. 96 to the 3' end of SEQ ID NO 90.
   The bifunctional fused aptamer of (SEQ ID NO 106) was constructed by:
1) Adding SEQ ID NO 90 to the 3' end of SEQ ID NO 97.

I claim:

1. An infectious agent bifunctional aptamer comprising a first sequence component, and a second sequence component, wherein the first sequence component is a complement binding sequence component selected from the group consisting of SEQ ID NOs 1-14, 16-25, 28-30, 32, 36, 37, 39, 42-44, 46, 48-56, 58-62, 64-68, 70, 71, 74, 76, and 83-87 and SEQ ID NOs 90-96, each having a 5' end and a 3' end, wherein the second sequence component binds to a specific infectious agent, and wherein the second sequence component sequence is inserted into the first sequence component from 1 to 5 bases from the 5' end of the first sequence component.

2. The infectious agent bifunctional allosteric aptamer of claim 1, wherein the infectious agent is selected from the group consisting of $PrP^C$, $PrP^{Sc}$, Transmissible spongiform encephalopathies (TSEs), Creutzfeldt-Jacob disease (CJD), variant CJD (vCJD), bovine spongiform encepathy (BSE), Chronic Wasting Disease (CWD), and scrapie.

3. The infectious agent bifunctional aptamer of claim 1, wherein the infectious agent is $PrP^{Sc}$ and the sequence of the second sequence component is SEQ ID NO. 90.

4. A neurodegenerative disease bifunctional aptamer comprising a first sequence component, and a second sequence component, wherein the first sequence component is a complement binding sequence component selected from the group consisting of SEQ ID NOs 1-1-14, 16-25, 28-30, 32, 36, 37, 39, 42-44, 46, 48-56, 58-62, 64-68, 70, 71, 74, 76, and 83-87 and SEQ ID NOs 90-96, each having a 5' end and a 3' end, wherein the second sequence component binds to a specific infectious agent, and wherein the second sequence component sequence is inserted into the first sequence component from 1 to 5 bases from the 5' end.

5. The neurodegenerative disease bifunctional aptamer of claim 4, wherein the neurodegenerative disease is selected from the group consisting of Alzheimer's Disease, mild cognitive impairment, Parkinson's disease, and other neurodegenerative diseases.

6. The neurodegenerative disease bifunctional aptamer of claim 4, wherein the neurodegenerative disease is Alzheimer's Disease and the sequence of the second sequence component is SEQ ID NO. 91.

\* \* \* \* \*

SEQUENCE LISTING

<160> NUMBER OF SEQ ID NOS: 106

<210> SEQ ID NO 1
<211> LENGTH: 54
<212> TYPE: RNA
<213> ORGANISM: Artificial sequence
<220> FEATURE:
<223> OTHER INFORMATION: Synthetic

<400> SEQUENCE: 1
uagcgacaag gcgacaagca augacacauu aacagacccu gguuagugaa cgaa      54

<210> SEQ ID NO 2
<211> LENGTH: 54
<212> TYPE: RNA
<213> ORGANISM: Artificial sequence
<220> FEATURE:
<223> OTHER INFORMATION: Synthetic

<400> SEQUENCE: 2
aaggcgaggu gcgacccgca cguggcaucu gauagcacau gaaaaggcac guca      54

<210> SEQ ID NO 3
<211> LENGTH: 55
<212> TYPE: RNA
<213> ORGANISM: Artificial sequence
<220> FEATURE:
<223> OTHER INFORMATION: Synthetic

<400> SEQUENCE: 3
ucuuccaacg accaugcggc gacaagcgac uacaagaggg uacccacgga cagca     55

<210> SEQ ID NO 4
<211> LENGTH: 54
<212> TYPE: RNA
<213> ORGANISM: Artificial sequence
<220> FEATURE:
<223> OTHER INFORMATION: Synthetic

<400> SEQUENCE: 4
uggcgacgag gcggcaggca augacacauu agcagacccu gguuaaugag cgaa        54

<210> SEQ ID NO 5
<211> LENGTH: 54
<212> TYPE: RNA
<213> ORGANISM: Artificial sequence
<220> FEATURE:
<223> OTHER INFORMATION: Synthetic

<400> SEQUENCE: 5
uagcgacaag gcgacaagca augacacauu aacggacccu gguuaaugaa cgaa        54

<210> SEQ ID NO 6
<211> LENGTH: 56
<212> TYPE: RNA
<213> ORGANISM: Artificial sequence
<220> FEATURE:
<223> OTHER INFORMATION: Synthetic

<400> SEQUENCE: 6
uggcggauac ucugcgaagg gcgaacccaa cauuucgcac aggaccgacu acugca       56

<210> SEQ ID NO 7
<211> LENGTH: 56
<212> TYPE: RNA
<213> ORGANISM: Artificial sequence
<220> FEATURE:
<223> OTHER INFORMATION: Synthetic

<400> SEQUENCE: 7
uggcggauac ucugcgaagg gcgaacccaa cauuucgcac agaaccgacu acugca       56

<210> SEQ ID NO 8
<211> LENGTH: 54
<212> TYPE: RNA
<213> ORGANISM: Artificial sequence
<220> FEATURE:
<223> OTHER INFORMATION: Synthetic

<400> SEQUENCE: 8
aagcgacaag gcgacaagca augacacauu aacagacccu gguuaaugga cgac        54

<210> SEQ ID NO 9
<211> LENGTH: 54
<212> TYPE: RNA
<213> ORGANISM: Artificial sequence
<220> FEATURE:
<223> OTHER INFORMATION: Synthetic

<400> SEQUENCE: 9
aggcgacaag gcgacaagca augucacauu aacagacccu gguuaaugaa cgaa        54

<210> SEQ ID NO 10
<211> LENGTH: 54
<212> TYPE: RNA
<213> ORGANISM: Artificial sequence
<220> FEATURE:
<223> OTHER INFORMATION: Synthetic

<400> SEQUENCE: 10
uagcgacaag gcgacaggca augguacauu aacagacccu gguuaaugaa cgaa        54

<210> SEQ ID NO 11
<211> LENGTH: 54
<212> TYPE: RNA
<213> ORGANISM: Artificial sequence

```
<220> FEATURE:
<223> OTHER INFORMATION: Synthetic

<400> SEQUENCE: 11
uagcgacaag gcgacgagca acgacacauu aacagacccc gguuaaugaa cgaa        54

<210> SEQ ID NO 12
<211> LENGTH: 54
<212> TYPE: RNA
<213> ORGANISM: Artificial sequence
<220> FEATURE:
<223> OTHER INFORMATION: Synthetic

<400> SEQUENCE: 12
uagcgagaag gcgacaagca acgacacauu aacagacccu gguuaaugga cgaa        54

<210> SEQ ID NO 13
<211> LENGTH: 54
<212> TYPE: RNA
<213> ORGANISM: Artificial sequence
<220> FEATURE:
<223> OTHER INFORMATION: Synthetic

<400> SEQUENCE: 13
uagcgccgag gcgacaggcg acgacacauu aacagacccu gguuaaugag ugaa        54

<210> SEQ ID NO 14
<211> LENGTH: 56
<212> TYPE: RNA
<213> ORGANISM: Artificial sequence
<220> FEATURE:
<223> OTHER INFORMATION: Synthetic

<400> SEQUENCE: 14
uagcggacac ucugcgaagg gcgaacccaa cauuucgcac ggaaccgacu acuaca      56

<210> SEQ ID NO 15
<211> LENGTH: 55
<212> TYPE: RNA
<213> ORGANISM: Artificial sequence
<220> FEATURE:
<223> OTHER INFORMATION: Synthetic

<400> SEQUENCE: 15
uccgaucuuc auacccgcga ccggcgacau ugugaccgca aaaccggaca acccc       55

<210> SEQ ID NO 16
<211> LENGTH: 55
<212> TYPE: RNA
<213> ORGANISM: Artificial sequence
<220> FEATURE:
<223> OTHER INFORMATION: Synthetic

<400> SEQUENCE: 16
uggcgauacu cugcgaaggg cgaacccaac auuucgcaca gaaccgacua cugca       55

<210> SEQ ID NO 17
<211> LENGTH: 55
<212> TYPE: RNA
<213> ORGANISM: Artificial sequence
<220> FEATURE:
<223> OTHER INFORMATION: Synthetic

<400> SEQUENCE: 17
aaggcgaggc gcgacccgca cgugacaucc gauaccacgu gaaaaaggca cgaca       55
```

```
<210> SEQ ID NO 18
<211> LENGTH: 54
<212> TYPE: RNA
<213> ORGANISM: Artificial sequence
<220> FEATURE:
<223> OTHER INFORMATION: Synthetic

<400> SEQUENCE: 18
uagcgacaag gcgacaagca acgacacauu aacagacccu gguuaaugaa cgaa        54

<210> SEQ ID NO 19
<211> LENGTH: 54
<212> TYPE: RNA
<213> ORGANISM: Artificial sequence
<220> FEATURE:
<223> OTHER INFORMATION: Synthetic

<400> SEQUENCE: 19
uagcgacaag gcgacaggca acgacgcauu aacagacccu gguugaugaa cgaa        54

<210> SEQ ID NO 20
<211> LENGTH: 54
<212> TYPE: RNA
<213> ORGANISM: Artificial sequence
<220> FEATURE:
<223> OTHER INFORMATION: Synthetic

<400> SEQUENCE: 20
uagcgacaag gcgacaggca augacacauu aauagacccu gguuaaugaa cgaa        54

<210> SEQ ID NO 21
<211> LENGTH: 54
<212> TYPE: RNA
<213> ORGANISM: Artificial sequence
<220> FEATURE:
<223> OTHER INFORMATION: Synthetic

<400> SEQUENCE: 21
uagcgacaag gcgacgagca auggcacauu aacagacccu gguuaagaa cggg         54

<210> SEQ ID NO 22
<211> LENGTH: 54
<212> TYPE: RNA
<213> ORGANISM: Artificial sequence
<220> FEATURE:
<223> OTHER INFORMATION: Synthetic

<400> SEQUENCE: 22
uagcgacaag gcggcaagca acgacgcauu aacagacccu gguuaaugaa ugaa        54

<210> SEQ ID NO 23
<211> LENGTH: 54
<212> TYPE: RNA
<213> ORGANISM: Artificial sequence
<220> FEATURE:
<223> OTHER INFORMATION: Synthetic

<400> SEQUENCE: 23
uagcgacggu gcgacaagca auggcacauu aacagacccu gguuaaugaa cgaa        54

<210> SEQ ID NO 24
<211> LENGTH: 54
<212> TYPE: RNA
<213> ORGANISM: Artificial sequence
<220> FEATURE:
<223> OTHER INFORMATION: Synthetic
```

<400> SEQUENCE: 24
uagcgacuag gcgacaagca augacacauu aacagacccu gguuaaugaa cgaa         54

<210> SEQ ID NO 25
<211> LENGTH: 54
<212> TYPE: RNA
<213> ORGANISM: Artificial sequence
<220> FEATURE:
<223> OTHER INFORMATION: Synthetic

<400> SEQUENCE: 25
uaggcgaggc gcgacccgca cgugacaucu gauagcacgu gaaaagacac uaca         54

<210> SEQ ID NO 26
<211> LENGTH: 55
<212> TYPE: RNA
<213> ORGANISM: Artificial sequence
<220> FEATURE:
<223> OTHER INFORMATION: Synthetic

<400> SEQUENCE: 26
ugauuggaau ucuuggggcc gagcgacccg gccguguaug agacaagauu acucc        55

<210> SEQ ID NO 27
<211> LENGTH: 55
<212> TYPE: RNA
<213> ORGANISM: Artificial sequence
<220> FEATURE:
<223> OTHER INFORMATION: Synthetic

<400> SEQUENCE: 27
uggaguuuga uugcgaccgg ggcgacaccc acaaaggcga caaaaucauu cacac        55

<210> SEQ ID NO 28
<211> LENGTH: 54
<212> TYPE: RNA
<213> ORGANISM: Artificial sequence
<220> FEATURE:
<223> OTHER INFORMATION: Synthetic

<400> SEQUENCE: 28
uggcgacaag gcgacaagca augacacauu aacagacccu gguuaaugaa cgua         54

<210> SEQ ID NO 29
<211> LENGTH: 56
<212> TYPE: RNA
<213> ORGANISM: Artificial sequence
<220> FEATURE:
<223> OTHER INFORMATION: Synthetic

<400> SEQUENCE: 29
uggcggauac ucugcgaagg gcgaacccaa cauuucgcac agaaccggcu acucca       56

<210> SEQ ID NO 30
<211> LENGTH: 56
<212> TYPE: RNA
<213> ORGANISM: Artificial sequence
<220> FEATURE:
<223> OTHER INFORMATION: Synthetic

<400> SEQUENCE: 30
uggcggcuac ucugcgaagg gcgaacccaa cauuucgcac agaaccgacu acugca       56

<210> SEQ ID NO 31

```
<211> LENGTH: 54
<212> TYPE: RNA
<213> ORGANISM: Artificial sequence
<220> FEATURE:
<223> OTHER INFORMATION: Synthetic

<400> SEQUENCE: 31
uugcucguac ccugggagca aagaccugau cagacccaac agaucuaaca agca         54

<210> SEQ ID NO 32
<211> LENGTH: 54
<212> TYPE: RNA
<213> ORGANISM: Artificial sequence
<220> FEATURE:
<223> OTHER INFORMATION: Synthetic

<400> SEQUENCE: 32
aagcgacgag gcgacaagca augacacauu aacagacccu gguuaaugga cgaa         54

<210> SEQ ID NO 33
<211> LENGTH: 55
<212> TYPE: RNA
<213> ORGANISM: Artificial sequence
<220> FEATURE:
<223> OTHER INFORMATION: Synthetic

<400> SEQUENCE: 33
acgguggcgc gggcggaccc aaaaugacgc cacaaagaag gcaacacaga aaaca        55

<210> SEQ ID NO 34
<211> LENGTH: 54
<212> TYPE: RNA
<213> ORGANISM: Artificial sequence
<220> FEATURE:
<223> OTHER INFORMATION: Synthetic

<400> SEQUENCE: 34
acgguggcgc gggcggaccc aaaaugacgc cacaaagaag gcaacacaga aaca         54

<210> SEQ ID NO 35
<211> LENGTH: 54
<212> TYPE: RNA
<213> ORGANISM: Artificial sequence
<220> FEATURE:
<223> OTHER INFORMATION: Synthetic

<400> SEQUENCE: 35
cagcgacaag gcgacaagca auagacacgu uaacagacac ugguuaauga acga         54

<210> SEQ ID NO 36
<211> LENGTH: 54
<212> TYPE: RNA
<213> ORGANISM: Artificial sequence
<220> FEATURE:
<223> OTHER INFORMATION: Synthetic

<400> SEQUENCE: 36
cagcgacgag gcgacaggca acgacacauu aacagacccc gguuaaugag cgaa         54

<210> SEQ ID NO 37
<211> LENGTH: 54
<212> TYPE: RNA
<213> ORGANISM: Artificial sequence
<220> FEATURE:
<223> OTHER INFORMATION: Synthetic

<400> SEQUENCE: 37
```
cugcgacaag gcgacaagca acgacacauu aacaggcccu gguuaaugaa cgga          54

<210> SEQ ID NO 38
<211> LENGTH: 54
<212> TYPE: RNA
<213> ORGANISM: Artificial sequence
<220> FEATURE:
<223> OTHER INFORMATION: Synthetic

<400> SEQUENCE: 38
gacaguauuu gcggggcaag ggcgcgacaa caaacacaag uacagaaaag gcua          54

<210> SEQ ID NO 39
<211> LENGTH: 54
<212> TYPE: RNA
<213> ORGANISM: Artificial sequence
<220> FEATURE:
<223> OTHER INFORMATION: Synthetic

<400> SEQUENCE: 39
gagcgacgag gcgucaagca augacacauu aacagacccu ggcuaaugaa ugaa          54

<210> SEQ ID NO 40
<211> LENGTH: 55
<212> TYPE: RNA
<213> ORGANISM: Artificial sequence
<220> FEATURE:
<223> OTHER INFORMATION: Synthetic

<400> SEQUENCE: 40
gcugagggcg gcgaccagua caugcagcga caaauguaca cacaagcgac gaaaa         55

<210> SEQ ID NO 41
<211> LENGTH: 54
<212> TYPE: RNA
<213> ORGANISM: Artificial sequence
<220> FEATURE:
<223> OTHER INFORMATION: Synthetic

<400> SEQUENCE: 41
uaccuuauuc cgcccccgcu gcccuggacg uggagacucu gaaacuccag cuau          54

<210> SEQ ID NO 42
<211> LENGTH: 54
<212> TYPE: RNA
<213> ORGANISM: Artificial sequence
<220> FEATURE:
<223> OTHER INFORMATION: Synthetic

<400> SEQUENCE: 42
uagcaacaag gcgacaggca augacacauu aacagaaccu gguuaaagaa cgaa          54

<210> SEQ ID NO 43
<211> LENGTH: 54
<212> TYPE: RNA
<213> ORGANISM: Artificial sequence
<220> FEATURE:
<223> OTHER INFORMATION: Synthetic

<400> SEQUENCE: 43
uagcaacaag gcgacuagca acgacacauu aacaggcccu gguuaaugga cgaa          54

<210> SEQ ID NO 44
<211> LENGTH: 54
<212> TYPE: RNA

```
<213> ORGANISM: Artificial sequence
<220> FEATURE:
<223> OTHER INFORMATION: Synthetic

<400> SEQUENCE: 44
uagcaacaag gcgauaagca auggcacauu aacuggcccu gguuaaugaa cgaa        54

<210> SEQ ID NO 45
<211> LENGTH: 55
<212> TYPE: RNA
<213> ORGANISM: Artificial sequence
<220> FEATURE:
<223> OTHER INFORMATION: Synthetic

<400> SEQUENCE: 45
uagcgacaag gcgacaaagc aaugacacau uaacggaccc ugguuaauga acgaa       55

<210> SEQ ID NO 46
<211> LENGTH: 54
<212> TYPE: RNA
<213> ORGANISM: Artificial sequence
<220> FEATURE:
<223> OTHER INFORMATION: Synthetic

<400> SEQUENCE: 46
uagcgacaag gcgacaagca acgacacauu aacagacccu ggcuaaugac gaaa        54

<210> SEQ ID NO 47
<211> LENGTH: 54
<212> TYPE: RNA
<213> ORGANISM: Artificial sequence
<220> FEATURE:
<223> OTHER INFORMATION: Synthetic

<400> SEQUENCE: 47
uagcgacaag gcgacaagca acgacacauu aacagacccu guuaaugaac gaaa        54

<210> SEQ ID NO 48
<211> LENGTH: 54
<212> TYPE: RNA
<213> ORGANISM: Artificial sequence
<220> FEATURE:
<223> OTHER INFORMATION: Synthetic

<400> SEQUENCE: 48
uagcgacaag gcgacaagca acgacacauu aacggacccu gguuaaugga cgaa        54

<210> SEQ ID NO 49
<211> LENGTH: 54
<212> TYPE: RNA
<213> ORGANISM: Artificial sequence
<220> FEATURE:
<223> OTHER INFORMATION: Synthetic

<400> SEQUENCE: 49
uagcgacaag gcgacaagca acgacacguu aacagacccu gguuaaugaa cgaa        54

<210> SEQ ID NO 50
<211> LENGTH: 54
<212> TYPE: RNA
<213> ORGANISM: Artificial sequence
<220> FEATURE:
<223> OTHER INFORMATION: Synthetic

<400> SEQUENCE: 50
uagcgacaag gcgacaagca augacacauu aacagacccu gguuaaugaa cgaa        54
```

```
<210> SEQ ID NO 51
<211> LENGTH: 54
<212> TYPE: RNA
<213> ORGANISM: Artificial sequence
<220> FEATURE:
<223> OTHER INFORMATION: Synthetic

<400> SEQUENCE: 51
uagcgacaag gcgacaagca augacacauu aacagacccu gguuaaugaa cgag        54

<210> SEQ ID NO 52
<211> LENGTH: 54
<212> TYPE: RNA
<213> ORGANISM: Artificial sequence
<220> FEATURE:
<223> OTHER INFORMATION: Synthetic

<400> SEQUENCE: 52
uagcgacaag gcgacaagca augacacauu aauagacccu gguuaaugga cgaa        54

<210> SEQ ID NO 53
<211> LENGTH: 54
<212> TYPE: RNA
<213> ORGANISM: Artificial sequence
<220> FEATURE:
<223> OTHER INFORMATION: Synthetic

<400> SEQUENCE: 53
uagcgacaag gcgacaagca augacccauu aacaggcccu gguuaaucaa cgaa        54

<210> SEQ ID NO 54
<211> LENGTH: 54
<212> TYPE: RNA
<213> ORGANISM: Artificial sequence
<220> FEATURE:
<223> OTHER INFORMATION: Synthetic

<400> SEQUENCE: 54
uagcgacaag gcgacaagca auggcacauu aacagacccu gguuaacgaa cgaa        54

<210> SEQ ID NO 55
<211> LENGTH: 54
<212> TYPE: RNA
<213> ORGANISM: Artificial sequence
<220> FEATURE:
<223> OTHER INFORMATION: Synthetic

<400> SEQUENCE: 55
uagcgacaag gcgacaagca auggcacauu gacagacccu gguuaaugag agaa        54

<210> SEQ ID NO 56
<211> LENGTH: 54
<212> TYPE: RNA
<213> ORGANISM: Artificial sequence
<220> FEATURE:
<223> OTHER INFORMATION: Synthetic

<400> SEQUENCE: 56
uagcgacaag gcgacaagcg augacacauu aacaggcccu gguuaaugaa ugaa        54

<210> SEQ ID NO 57
<211> LENGTH: 55
<212> TYPE: RNA
<213> ORGANISM: Artificial sequence
<220> FEATURE:
```

<223> OTHER INFORMATION: Synthetic

<400> SEQUENCE: 57
uagcgacaag gcgacaggca augacacauu aaauagaccc ugguuaauga acgaa         55

<210> SEQ ID NO 58
<211> LENGTH: 54
<212> TYPE: RNA
<213> ORGANISM: Artificial sequence
<220> FEATURE:
<223> OTHER INFORMATION: Synthetic

<400> SEQUENCE: 58
uagcgacaag gcgacaggca augacacauu aacagacccu gguuaaugaa cgaa          54

<210> SEQ ID NO 59
<211> LENGTH: 54
<212> TYPE: RNA
<213> ORGANISM: Artificial sequence
<220> FEATURE:
<223> OTHER INFORMATION: Synthetic

<400> SEQUENCE: 59
uagcgacaag gcgacaggca augacacauu aacagacccu gguuaaugaa ugaa          54

<210> SEQ ID NO 60
<211> LENGTH: 54
<212> TYPE: RNA
<213> ORGANISM: Artificial sequence
<220> FEATURE:
<223> OTHER INFORMATION: Synthetic

<400> SEQUENCE: 60
uagcgacaag gcgacaggca augacacauu aacaggcccu gguuaaugaa cgaa          54

<210> SEQ ID NO 61
<211> LENGTH: 54
<212> TYPE: RNA
<213> ORGANISM: Artificial sequence
<220> FEATURE:
<223> OTHER INFORMATION: Synthetic

<400> SEQUENCE: 61
uagcgacaag gcgacaggca augacacauu agcggacccu gguuaaugaa cgaa          54

<210> SEQ ID NO 62
<211> LENGTH: 54
<212> TYPE: RNA
<213> ORGANISM: Artificial sequence
<220> FEATURE:
<223> OTHER INFORMATION: Synthetic

<400> SEQUENCE: 62
uagcgacaag gcgacaggca augccucauu agcagacccu gguuaaugaa caaa          54

<210> SEQ ID NO 63
<211> LENGTH: 56
<212> TYPE: RNA
<213> ORGANISM: Artificial sequence
<220> FEATURE:
<223> OTHER INFORMATION: Synthetic

<400> SEQUENCE: 63
uagcgacaag gcgacgagca aauggcacau uaacagaccc ugguuaauga acgaaa        56

<210> SEQ ID NO 64
<211> LENGTH: 54
<212> TYPE: RNA
<213> ORGANISM: Artificial sequence
<220> FEATURE:
<223> OTHER INFORMATION: Synthetic

<400> SEQUENCE: 64
uagcgacaag gcgacgggca augacccauu aacagacccu gguuaaugaa cgaa        54

<210> SEQ ID NO 65
<211> LENGTH: 54
<212> TYPE: RNA
<213> ORGANISM: Artificial sequence
<220> FEATURE:
<223> OTHER INFORMATION: Synthetic

<400> SEQUENCE: 65
uagcgacaag gcggcaggca auaacacauu aacagacccc gguuaaugaa cgaa        54

<210> SEQ ID NO 66
<211> LENGTH: 54
<212> TYPE: RNA
<213> ORGANISM: Artificial sequence
<220> FEATURE:
<223> OTHER INFORMATION: Synthetic

<400> SEQUENCE: 66
uagcgacaag gcggcgagca augacacauu aacggacccu gguuaaugaa caaa        54

<210> SEQ ID NO 67
<211> LENGTH: 56
<212> TYPE: RNA
<213> ORGANISM: Artificial sequence
<220> FEATURE:
<223> OTHER INFORMATION: Synthetic

<400> SEQUENCE: 67
uagcgacuag gcgacaagca augacacauu aacagacccu gguuaaaucg aacgaa      56

<210> SEQ ID NO 68
<211> LENGTH: 54
<212> TYPE: RNA
<213> ORGANISM: Artificial sequence
<220> FEATURE:
<223> OTHER INFORMATION: Synthetic

<400> SEQUENCE: 68
uagcgacuag gcgacgggca augacgcauu aacaggcccu gguuaaugaa caga        54

<210> SEQ ID NO 69
<211> LENGTH: 56
<212> TYPE: RNA
<213> ORGANISM: Artificial sequence
<220> FEATURE:
<223> OTHER INFORMATION: Synthetic

<400> SEQUENCE: 69
uaggcgaggc gcgacccgcg cgggacaucu gauagcacgu gaaaaauggc acaacg      56

<210> SEQ ID NO 70
<211> LENGTH: 54
<212> TYPE: RNA
<213> ORGANISM: Artificial sequence
<220> FEATURE:
<223> OTHER INFORMATION: Synthetic

<400> SEQUENCE: 70
uaggcgaggc gcgacccgcg cgugacaucu gauagcacgu gaaaaggcac gaca        54

<210> SEQ ID NO 71
<211> LENGTH: 55
<212> TYPE: RNA
<213> ORGANISM: Artificial sequence
<220> FEATURE:
<223> OTHER INFORMATION: Synthetic

<400> SEQUENCE: 71
uaggcgaggc gggacccgca cgugacaucu gauagcacgu gaaaaggcac gacaa       55

<210> SEQ ID NO 72
<211> LENGTH: 54
<212> TYPE: RNA
<213> ORGANISM: Artificial sequence
<220> FEATURE:
<223> OTHER INFORMATION: Synthetic

<400> SEQUENCE: 72
ucaauaaaug gcagaccuga ugcugcgggc guaaggcaua gcgaccaaca uucu        54

<210> SEQ ID NO 73
<211> LENGTH: 55
<212> TYPE: RNA
<213> ORGANISM: Artificial sequence
<220> FEATURE:
<223> OTHER INFORMATION: Synthetic

<400> SEQUENCE: 73
uccccgauac ugcgaccaac agauuaccag ggcgaacagc gaccgagcaa caaug       55

<210> SEQ ID NO 74
<211> LENGTH: 55
<212> TYPE: RNA
<213> ORGANISM: Artificial sequence
<220> FEATURE:
<223> OTHER INFORMATION: Synthetic

<400> SEQUENCE: 74
uccucaaagc gaccgaccuu ugccuaaaca gcugaugguu uacaaaggaa gcacg       55

<210> SEQ ID NO 75
<211> LENGTH: 56
<212> TYPE: RNA
<213> ORGANISM: Artificial sequence
<220> FEATURE:
<223> OTHER INFORMATION: Synthetic

<400> SEQUENCE: 75
uccuucccca augcgacacc ccagcaaggc gacagcuggc caggcgacaa acaaaa      56

<210> SEQ ID NO 76
<211> LENGTH: 54
<212> TYPE: RNA
<213> ORGANISM: Artificial sequence
<220> FEATURE:
<223> OTHER INFORMATION: Synthetic

<400> SEQUENCE: 76
ucgcgacaag gcgacgagca auggcacauu aacagacccu gguuaaugaa cgaa        54

<210> SEQ ID NO 77
<211> LENGTH: 55

```
<212> TYPE: RNA
<213> ORGANISM: Artificial sequence
<220> FEATURE:
<223> OTHER INFORMATION: Synthetic

<400> SEQUENCE: 77
ucugagggcg gcggccagua caugcagcga caaaauguac acacaagcga caaaa       55

<210> SEQ ID NO 78
<211> LENGTH: 55
<212> TYPE: RNA
<213> ORGANISM: Artificial sequence
<220> FEATURE:
<223> OTHER INFORMATION: Synthetic

<400> SEQUENCE: 78
ucuggcgagg gcggcuaggg gacacagcgu agucugauga cgcagagcaa ucuaa       55

<210> SEQ ID NO 79
<211> LENGTH: 55
<212> TYPE: RNA
<213> ORGANISM: Artificial sequence
<220> FEATURE:
<223> OTHER INFORMATION: Synthetic

<400> SEQUENCE: 79
uggcgaagac ccgaacaccc ugagcuguuu aaaggcgacg acgcagcgac gagcc       55

<210> SEQ ID NO 80
<211> LENGTH: 55
<212> TYPE: RNA
<213> ORGANISM: Artificial sequence
<220> FEATURE:
<223> OTHER INFORMATION: Synthetic

<400> SEQUENCE: 80
uggcgaagac ccgaucaccc ugagcuguuu aaaggcgacg acgcagcgac gagcc       55

<210> SEQ ID NO 81
<211> LENGTH: 55
<212> TYPE: RNA
<213> ORGANISM: Artificial sequence
<220> FEATURE:
<223> OTHER INFORMATION: Synthetic

<400> SEQUENCE: 81
uggcgacaag gcgacaaagc aaugacacau uaacagaccc ugguuaauga acgua       55

<210> SEQ ID NO 82
<211> LENGTH: 55
<212> TYPE: RNA
<213> ORGANISM: Artificial sequence
<220> FEATURE:
<223> OTHER INFORMATION: Synthetic

<400> SEQUENCE: 82
uggcgacaag gcgacaggca augaacacau uaacggaccc ugguuaauga acgaa       55

<210> SEQ ID NO 83
<211> LENGTH: 54
<212> TYPE: RNA
<213> ORGANISM: Artificial sequence
<220> FEATURE:
<223> OTHER INFORMATION: Synthetic

<400> SEQUENCE: 83
```
uggcgacaag gcgacaggca augacacauu aacggacccu gguuaaugaa cgaa    54

<210> SEQ ID NO 84
<211> LENGTH: 56
<212> TYPE: RNA
<213> ORGANISM: Artificial sequence
<220> FEATURE:
<223> OTHER INFORMATION: Synthetic

<400> SEQUENCE: 84
uggcggauac gcugcgaagg gcgaacccaa cauuucgcac agagccgacu acugcc    56

<210> SEQ ID NO 85
<211> LENGTH: 56
<212> TYPE: RNA
<213> ORGANISM: Artificial sequence
<220> FEATURE:
<223> OTHER INFORMATION: Synthetic

<400> SEQUENCE: 85
uggcggauac ucugcgaagg gcgaacacaa cauuucgcac agaaccgacu acugca    56

<210> SEQ ID NO 86
<211> LENGTH: 56
<212> TYPE: RNA
<213> ORGANISM: Artificial sequence
<220> FEATURE:
<223> OTHER INFORMATION: Synthetic

<400> SEQUENCE: 86
uggcggauac ucugcgaagg gcgaacccaa caucucgcac agaaccgacu acugcg    56

<210> SEQ ID NO 87
<211> LENGTH: 56
<212> TYPE: RNA
<213> ORGANISM: Artificial sequence
<220> FEATURE:
<223> OTHER INFORMATION: Synthetic

<400> SEQUENCE: 87
uggcggauac ucugcgaagg gcgaacccaa cguuucgcac agaaccgacu acugcg    56

<210> SEQ ID NO 88
<211> LENGTH: 55
<212> TYPE: RNA
<213> ORGANISM: Artificial sequence
<220> FEATURE:
<223> OTHER INFORMATION: Synthetic

<400> SEQUENCE: 88
uugcucauac ccugagagca aagaucugau cagacccaac agaucuagca agcau    55

<210> SEQ ID NO 89
<211> LENGTH: 55
<212> TYPE: RNA
<213> ORGANISM: Artificial sequence
<220> FEATURE:
<223> OTHER INFORMATION: Synthetic

<400> SEQUENCE: 89
uugguggcgc gggcgaaccc aaaaugacgc cacaaagaag acaauacagg aagca    55

<210> SEQ ID NO 90
<211> LENGTH: 60
<212> TYPE: RNA
<213> ORGANISM: Artificial sequence
<220> FEATURE:
<223> OTHER INFORMATION: Synthetic

<400> SEQUENCE: 90
gggagacaag acuagacgcu caacuacgaa cucaugacac aaggaugcaa ucucaucccg    60

<210> SEQ ID NO 91
<211> LENGTH: 67
<212> TYPE: RNA
<213> ORGANISM: Artificial sequence
<220> FEATURE:
<223> OTHER INFORMATION: Synthetic

<400> SEQUENCE: 91
uuuaccguaa ggccugucuu cguuugacag cggcuuguug acccucacac uuuguaccug    60
cugccaa    67

<210> SEQ ID NO 92
<211> LENGTH: 50
<212> TYPE: RNA
<213> ORGANISM: Artificial sequence
<220> FEATURE:
<223> OTHER INFORMATION: Synthetic

<400> SEQUENCE: 92
uccucaaagc gaccgaccuu ugccuaaaca gcugaugguu uacaaaggaa    50

<210> SEQ ID NO 93
<211> LENGTH: 50
<212> TYPE: RNA
<213> ORGANISM: Artificial sequence
<220> FEATURE:
<223> OTHER INFORMATION: Synthetic

<400> SEQUENCE: 93
aaagcgaccg accuuugccu aaacagcuga ugguuuacaa aggaagcacg    50

<210> SEQ ID NO 94
<211> LENGTH: 45
<212> TYPE: RNA
<213> ORGANISM: Artificial sequence
<220> FEATURE:
<223> OTHER INFORMATION: Synthetic

<400> SEQUENCE: 94
aaagcgaccg accuuugccu aaacagcuga ugguuuacaa aggaa    45

<210> SEQ ID NO 95
<211> LENGTH: 45
<212> TYPE: RNA
<213> ORGANISM: Artificial sequence
<220> FEATURE:
<223> OTHER INFORMATION: Synthetic

<400> SEQUENCE: 95
uccucaaagc gaccgaccuu ugccuaaaca gcugaugguu uacaa    45

<210> SEQ ID NO 96
<211> LENGTH: 45
<212> TYPE: RNA
<213> ORGANISM: Artificial sequence
<220> FEATURE:
<223> OTHER INFORMATION: Synthetic

<400> SEQUENCE: 96
gaccgaccuu ugccuaaaca gcugaugguu uacaaaggaa gcacg         45

<210> SEQ ID NO 97
<211> LENGTH: 115
<212> TYPE: RNA
<213> ORGANISM: Artificial sequence
<220> FEATURE:
<223> OTHER INFORMATION: Synthetic

<400> SEQUENCE: 97
uccucgggag acaagacuag acgcucaacu acgaacucau gacacaagga ugcaaucuca    60
ucccgaaagc gaccgaccuu ugccuaaaca gcugaugguu uacaaaggaa gcacg        115

<210> SEQ ID NO 98
<211> LENGTH: 110
<212> TYPE: RNA
<213> ORGANISM: Artificial sequence
<220> FEATURE:
<223> OTHER INFORMATION: Synthetic

<400> SEQUENCE: 98
uccucgggag acaagacuag acgcucaacu acgaacucau gacacaagga ugcaaucuca    60
ucccgaaagc gaccgaccuu ugccuaaaca gcugaugguu uacaaaggaa               110

<210> SEQ ID NO 99
<211> LENGTH: 110
<212> TYPE: RNA
<213> ORGANISM: Artificial sequence
<220> FEATURE:
<223> OTHER INFORMATION: Synthetic

<400> SEQUENCE: 99
aaagcgggag acaagacuag acgcucaacu acgaacucau gacacaagga ugcaaucuca    60
ucccggaccg accuuugccu aaacagcuga ugguuuacaa aggaagcacg              110

<210> SEQ ID NO 100
<211> LENGTH: 105
<212> TYPE: RNA
<213> ORGANISM: Artificial sequence
<220> FEATURE:
<223> OTHER INFORMATION: Synthetic

<400> SEQUENCE: 100
aaagcgggag acaagacuag acgcucaacu acgaacucau gacacaagga ugcaaucuca    60
ucccggaccg accuuugccu aaacagcuga ugguuuacaa aggaa                   105

<210> SEQ ID NO 101
<211> LENGTH: 105
<212> TYPE: RNA
<213> ORGANISM: Artificial sequence
<220> FEATURE:
<223> OTHER INFORMATION: Synthetic

<400> SEQUENCE: 101
aaagcgggag acaagacuag acgcucaacu acgaacucau gacacaagga ugcaaucuca    60
ucccggaccg accuuugccu aaacagcuga ugguuuacaa aggaa                   105

<210> SEQ ID NO 102
<211> LENGTH: 105
<212> TYPE: RNA
<213> ORGANISM: Artificial sequence
<220> FEATURE:
<223> OTHER INFORMATION: Synthetic

```
<400> SEQUENCE: 102
uccucgggag acaagacuag acgcucaacu acgaacucau gacacaagga ugcaaucuca        60
ucccgaaagc gaccgaccuu ugccuaaaca gcugaugguu uacaa                      105

<210> SEQ ID NO 103
<211> LENGTH: 105
<212> TYPE: RNA
<213> ORGANISM: Artificial sequence
<220> FEATURE:
<223> OTHER INFORMATION: Synthetic

<400> SEQUENCE: 103
gaccggggag acaagacuag acgcucaacu acgaacucau gacacaagga ugcaaucuca        60
ucccgaccuu ugccuaaaca gcugaugguu uacaaaggaa gcacg                      105

<210> SEQ ID NO 104
<211> LENGTH: 105
<212> TYPE: RNA
<213> ORGANISM: Artificial sequence
<220> FEATURE:
<223> OTHER INFORMATION: Synthetic

<400> SEQUENCE: 104
gggagacaag acuagacgcu caacuacgaa cucaugacac aaggaugcaa ucucaucccg        60
gaccgaccuu ugccuaaaca gcugaugguu uacaaaggaa gcacg                      105

<210> SEQ ID NO 105
<211> LENGTH: 105
<212> TYPE: RNA
<213> ORGANISM: Artificial sequence
<220> FEATURE:
<223> OTHER INFORMATION: Synthetic

<400> SEQUENCE: 105
gaccgaccuu ugccuaaaca gcugaugguu uacaaaggaa gcacggggag acaagacuag        60
acgcucaacu acgaacucau gacacaagga ugcaaucuca ucccg                      105

<210> SEQ ID NO 106
<211> LENGTH: 45
<212> TYPE: RNA
<213> ORGANISM: Artificial sequence
<220> FEATURE:
<223> OTHER INFORMATION: Synthetic

<400> SEQUENCE: 106
gaccgaccuu ugccuaaaca gcugaugguu uacaaaggaa gcacg                       45
```